United States Patent
Katoh et al.

(10) Patent No.: US 10,280,181 B2
(45) Date of Patent: May 7, 2019

(54) COLORING COMPOSITION, ANISOTROPIC LIGHT ABSORPTION FILM, LAMINATE, POLARIZING PLATE, IMAGE DISPLAY DEVICE AND COMPOUND

(71) Applicant: FUJIFILM Corporation, Tokyo (JP)

(72) Inventors: Takashi Katoh, Kanagawa (JP); Masatoshi Mizumura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/160,412

(22) Filed: May 20, 2016

(65) Prior Publication Data
US 2016/0340367 A1    Nov. 24, 2016

(30) Foreign Application Priority Data
May 22, 2015  (JP) .................................. 2015-104227

(51) Int. Cl.
C09K 19/34      (2006.01)
C07D 513/04    (2006.01)
(Continued)

(52) U.S. Cl.
CPC ............ *C07D 513/04* (2013.01); *C09B 31/30* (2013.01); *C09B 43/30* (2013.01); *C09B 43/32* (2013.01);
(Continued)

(58) Field of Classification Search
CPC ..................................................... C09K 19/30
See application file for complete search history.

(56) References Cited

U.S. PATENT DOCUMENTS

| 4,959,172 A | * | 9/1990 | Miura ..................... C09B 31/04 252/299.1 |
| 8,927,070 B2 | | 1/2015 | Iwahashi et al. |
| 2011/0177315 A1 | | 7/2011 | Iwahashi et al. |

FOREIGN PATENT DOCUMENTS

| JP | 2010001368 A | 1/2010 |
| JP | 2011237513 A | 11/2011 |

(Continued)

OTHER PUBLICATIONS

Office Action issued by the Japanese Patent Office dated Aug. 14, 2018, in connection with corresponding Japanese Patent Application No. 2015-104227.

*Primary Examiner* — Chanceity N Robinson
(74) *Attorney, Agent, or Firm* — Edwards Neils, LLC; Jean C. Edwards, Esq.

(57) ABSTRACT

A coloring composition containing one or more species of compounds represented by Formula (I) or Formula (II) below, wherein each of $R_1$ and $R_2$ represents a hydrogen atom or substituent, each of $Ar_1$ to $Ar_8$ independently represents an optionally substituted aromatic hydrocarbon group or optionally substituted heterocyclic group, and each of $L_1$ and $L_2$ independently represents a divalent linking group which interrupts π electron conjugated system:

Formula (I)

(Continued)

-continued

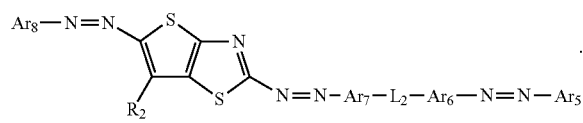

Formula (II)

17 Claims, 1 Drawing Sheet

(51) Int. Cl.
| | |
|---|---|
| C09B 56/02 | (2006.01) |
| C09K 19/60 | (2006.01) |
| G02B 5/30 | (2006.01) |
| H01L 51/52 | (2006.01) |
| C09K 19/24 | (2006.01) |
| C09D 133/10 | (2006.01) |
| C09D 133/14 | (2006.01) |
| C09B 31/30 | (2006.01) |
| C09B 43/30 | (2006.01) |
| C09B 43/32 | (2006.01) |
| C09B 69/10 | (2006.01) |
| C09K 19/04 | (2006.01) |

(52) U.S. Cl.
CPC ............ *C09B 56/02* (2013.01); *C09B 69/106* (2013.01); *C09B 69/107* (2013.01); *C09D 133/10* (2013.01); *C09D 133/14* (2013.01); *C09K 19/24* (2013.01); *C09K 19/3497* (2013.01); *C09K 19/601* (2013.01); *G02B 5/305* (2013.01); *G02B 5/3016* (2013.01); *G02B 5/3033* (2013.01); *H01L 51/5281* (2013.01); *C09K 2019/0448* (2013.01)

(56) References Cited

FOREIGN PATENT DOCUMENTS

JP  2013-109090 A  6/2013
JP  5412225 B2  11/2013

\* cited by examiner

COLORING COMPOSITION, ANISOTROPIC LIGHT ABSORPTION FILM, LAMINATE, POLARIZING PLATE, IMAGE DISPLAY DEVICE AND COMPOUND

CROSS-REFERENCE TO RELATED APPLICATIONS

The present application claims priority under 35 U.S.C. § 119 to Japanese Patent Application No. 2015-104227 filed May 22, 2015. The above application is hereby expressly incorporated by reference, in its entirety, into the present application.

BACKGROUND OF THE INVENTION

Field of the Invention

This invention relates to a coloring composition and a compound which has a high dichroic ratio. This invention further relates to an anisotropic light absorption film, a laminate, a polarizing plate and an image display device, using the coloring composition.

Background Art

For the scene where a function of attenuating, polarizing, scattering or shielding irradiated light including laser light and natural light is necessary, it has been a conventional practice to use a device which operates based on a principle differing from function to function. Products corresponded to these functions have therefore been manufactured by manufacturing processes again differing from function to function. For example, LCD (liquid crystal display) employs a linear polarizing plate or a circular polarizing plate, in order to control optical rotation or birefringence in display. The circular polarizing plate is also employed in OLED (organic light emitting diode), for the purpose of preventing reflection of external light. For these polarizing plates (polarizing elements), iodine has widely been used as a dichroic substance.

Alternatively, there has been discussed polarizing elements using organic dyes, in place of iodine, as the dichroic substance. For example, JP-A-2013-109090 describes a polarizing film composed of a composition which contains two or more species of dichroic dyes having different values of wavelength of maximum absorbance, wherein thienothiazole trisazo dye is used as the dichroic dye. JP-B2-5412225 describes an anisotropic light absorption film having a thienothiazole trisazo dye as the dichroic substance.
[PATENT DOCUMENT 1] JP-A-2013-109090
[PATENT DOCUMENT 2] JP-B2-5412225

The dichroic dyes described in JP-A-2013-109090 and JP-B2-5412225 have, how ver, been required for further improvement in dichroic ratio.

SUMMARY OF THE INVENTION

It is therefore an object of this invention to provide a compound having a high dichroic ratio, and a coloring composition using the compound. It is a further object of this invention to provide an anisotropic light absorption film, a laminate, a polarizing plate and an image display device, using the coloring composition.

After intensive studies for solving the problems described above, the present inventors found that a compound, having therein a thienothiazolylbisazo structure and a monoazo structure bound through a divalent linking group which interrupts the π electron conjugated system, can exhibit a high dichroic ratio. This invention was completed based on the finding.

According to this invention, the following inventions will be provided

[1] A coloring composition comprising one or more species of compounds represented by Formula (I) or Formula (II) below:

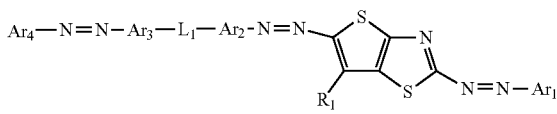

Formula (I)

in Formula (I), $R_1$ represents a hydrogen atom or substituent, each of $Ar_1$, $Ar_2$, $Ar_3$ and $Ar_4$ independently represents an optionally substituted aromatic hydrocarbon group or optionally substituted heterocyclic group, and $L_1$ represents a divalent linking group which interrupts π electron conjugated system;

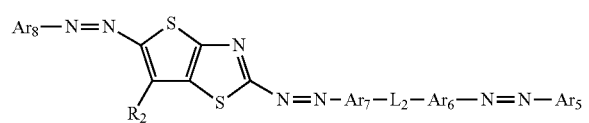

Formula (II)

in Formula (II), $R_2$ represents a hydrogen atom or substituent, each of $Ar_5$, $Ar_6$, $Ar_7$ and $Ar_8$ independently represents an optionally substituted aromatic hydrocarbon group or optionally substituted heterocyclic group, and $L_2$ represents a divalent linking group which interrupts electron conjugated system

[2] The coloring composition of [1], wherein in Formula (I) and Formula (II), each of $R_1$ and $R_2$ represents a hydrogen atom.

[3] The coloring composition of [1] or [2], wherein in Formula (I) and Formula (II), each of $L_1$ and $L_2$ represents —O(C=O)—, —(C=O)O—, —O—, —CH$_2$—, or combination thereof.

[4] The coloring composition of any one of [1] to [3], wherein the compound represented by Formula (I) or Formula (II) is a compound represented by Formula (IA) or (IIA) below:

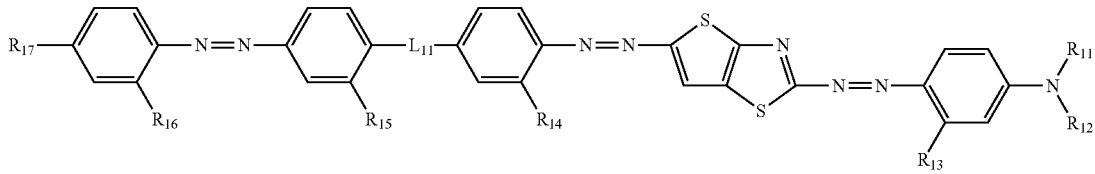

Formula (IA)

in Formula (IA), each of $R_{11}$ and $R_{12}$ independently represents an alkyl group having 1 to 6 carbon atoms or polymerizable group, each of $R_{13}$, $R_{14}$, $R_{15}$ and $R_{16}$ independently represents a hydrogen atom, alkyl group having 1 to 6 carbon atoms or alkoxy group having 1 to 6 carbon atoms, $R_{17}$ represents an alkyl group having 1 to 6 carbon atoms, alkoxy group having 1 to 6 carbon atoms, alkoxycarbonyl group having 2 to 6 carbon atoms, acyl group having 1 to 6 carbon atoms, or polymerizable group, and $L_{11}$ represents —O(C=O)—, —CH$_2$CH$_2$—, —CH$_2$O—, —(C=O)O—, or —O—;

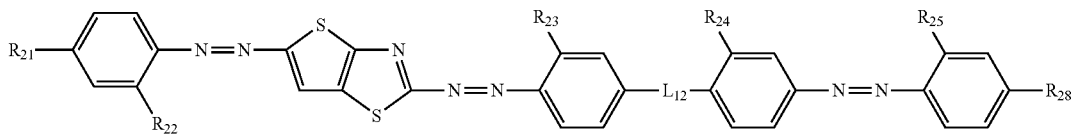

Formula (IIA)

in Formula (IIA), $R_{21}$ represents —N($R_{31}$)($R_{32}$), alkyl group having 1 to 6 carbon atoms, alkoxycarbonyl group having 2 to 6 carbon atoms, or polymerizable group, each of $R_{22}$, $R_{23}$, $R_{24}$ and $R_{25}$ independently represents a hydrogen atom, alkyl group having 1 to 6 carbon atoms or alkoxy group having 1 to 6 carbon atoms, $R_{26}$ represents an alkyl group having 1 to 6 carbon atoms, alkoxy group having 1 to 6 carbon atoms, alkoxycarbonyl group having 2 to 6 carbon atoms, or —N($R_{41}$)($R_{42}$), and $L_2$ represents —O(C=O)—, —CH$_2$CH$_2$—, —OCH$_2$—, or —(C=O)O—, where each of $R_{31}$ and $R_{32}$ independently represents an alkyl group having 1 to 6 carbon atoms or polymerizable group, and each of $R_{41}$ and $R_{42}$ independently represents an alkyl group having 1 to 6 carbon atoms.

[5] The coloring composition of any one of [1] to [4], further comprising one or more species of coloring compounds other than the compound represented by Formula (I) or Formula (II).

[6] The coloring composition of [5], wherein each of the one or more species of coloring compounds other than the compound represented by Formula (I) or Formula (II) have a wavelength of maximum absorbance of 400 to 600 nm.

[7] The coloring composition of [5] or [6], wherein each of the one or more species of coloring compounds other than the compound represented by Formula (I) or Formula (II) is a compound represented by Formula (III) or Formula (IV) below:

$$Ar_{14}—N=N—Ar_{13}—L_3—Ar_{12}—N=N—Ar_{11}$$

Formula (III)

in Formula (III), each of $Ar_{11}$, $Ar_{12}$, $Ar_{13}$ and $Ar_{14}$ independently represents an optionally substituted aromatic hydrocarbon group or optionally substituted heterocyclic group, and $L_3$ represents a divalent linking group, $$Ar_{16}—N=N—Ar_{15},$$

Formula (IV)

in Formula (IV), each of $Ar_{15}$ and $Ar_{16}$ independently represents an optionally substituted aromatic hydrocarbon group or optionally substituted heterocyclic group.

[8] The coloring composition of any one of [1] to [7], further comprising one or more species of thermotropic liquid crystalline polymer.

[9] The coloring composition of [8], wherein the thermotropic liquid crystalline polymer is a polymer at least having a repeating unit represented by any one of Formulae (IX-a), (IX-b) and (IX-c) below:

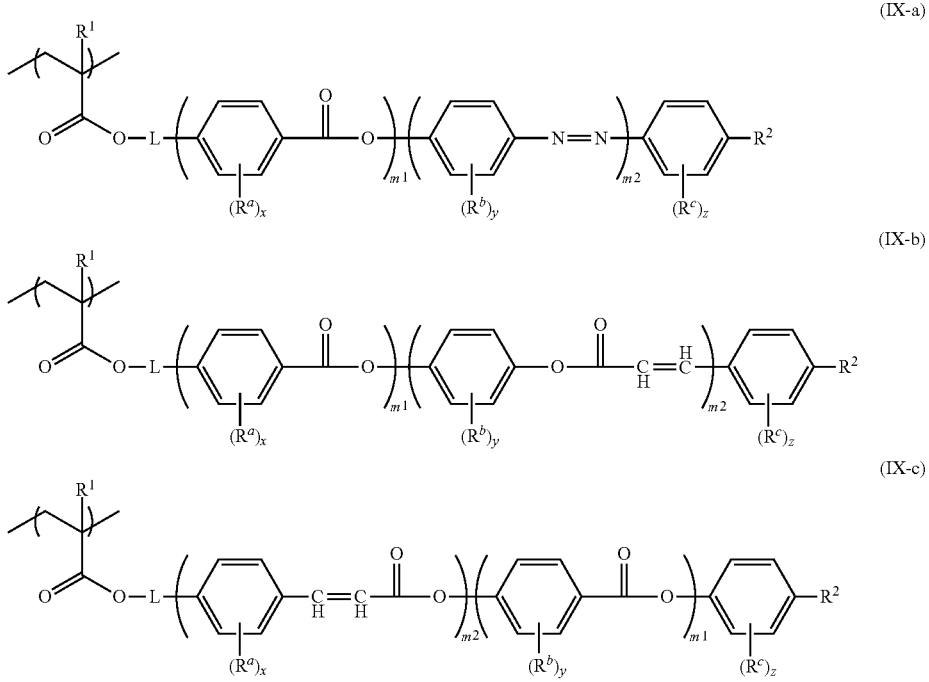

in Formulae (IX-a), (IX-b) and (IX-c), $R^1$ represents a hydrogen atom or methyl group; L represents a single bond, —$(CH_2)_{x1}O$— or —$(CH_2CH_2O)_{y1}$—, where x1 represents an integer of 2 to 10, y1 represents an integer of 1 to 5, $R^2$ represents a hydrogen atom, alkyl group having 1 to 10 carbon atoms, alkoxy group having 1 to 9 carbon atoms, cyano group, or optionally substituted amino group; m1 represents an integer of 0 to 2; m2 represents an integer of 1 to 2; each of $R^a$, $R^b$ and $R^c$ independently represents a substituent; and each of x, y and z independently represents an integer of 0 to 4.

[10] The coloring composition of any one of [1] to [9], further comprising a horizontal alignment agent

[11] An anisotropic light absorption film comprising the coloring composition of any one of [1] to [10].

[12] The anisotropic light absorption film of [11], which is formed on a surface of an alignment film.

[13] A laminate comprising an alignment film and the anisotropic light absorption film of [1].

[14] A polarizing plate comprising at least the anisotropic light absorption film of [11] or [12], or the laminate of [13].

[15] An image display device comprising the anisotropic light absorption film of [11] or [12], the laminate of [13], or the polarizing plate of [14].

[16] A compound represented by Formula (I) or Formula (II) below:

Formula (I)

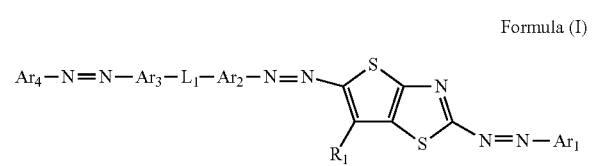

in Formula (I), $R_1$ represents a hydrogen atom, substituted or unsubstituted alkyl group, unsaturated hydrocarbon group, substituted or unsubstituted aryl group, substituted or unsubstituted heterocyclic group, halogen atom, cyano group, hydroxy group, substituted or unsubstituted carbamoyl group, substituted or unsubstituted sulfamoyl group, nitro group, substituted or unsubstituted alkoxy group, substituted or unsubstituted aryloxy group, substituted or unsubstituted acyl group, acyloxy group, alkoxyacyl group, acylamino group, substituted or unsubstituted sulfonyl group, amino group, or substituted amino group, each of $Ar_1$, $Ar_2$, $Ar_3$ and $Ar_4$ independently represents an optionally substituted aromatic hydrocarbon group or optionally substituted heterocyclic group, and $L_1$ represents a divalent linking group which interrupts π electron conjugated system;

Formula (II)

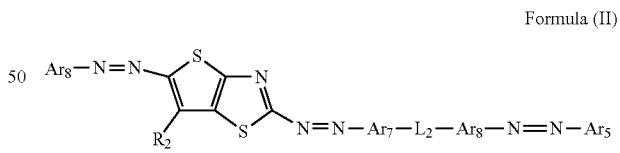

in Formula (II), $R_2$ represents a hydrogen atom, substituted or unsubstituted alkyl group, unsaturated hydrocarbon group, substituted or unsubstituted aryl group, substituted or unsubstituted heterocyclic group, halogen atom, cyano group, hydroxy group, substituted or unsubstituted carbamoyl group, substituted or unsubstituted sulfamoyl group, nitro group, substituted or unsubstituted alkoxy group, substituted or unsubstituted aryloxy group, substituted or unsubstituted acyl group, acyloxy group, alkoxyacyl group, acylamino group, substituted or unsubstituted sulfonyl group, amino group, or substituted amino group, each of $Ar_5$, $Ar_6$, $Ar_7$ and $Ar_8$ independently represents an optionally substituted aromatic hydrocarbon group or optionally substituted heterocyclic group, and $L_2$ represents a divalent linking group which interrupts electron conjugated system.

The compound, the coloring composition, the anisotropic light absorption film, the laminate, the polarizing plate, and the image display device of this invention have high levels of dichroic ratio.

DETAILED DESCRIPTION OF THE PREFERRED EMBODIMENTS

Figure 1:
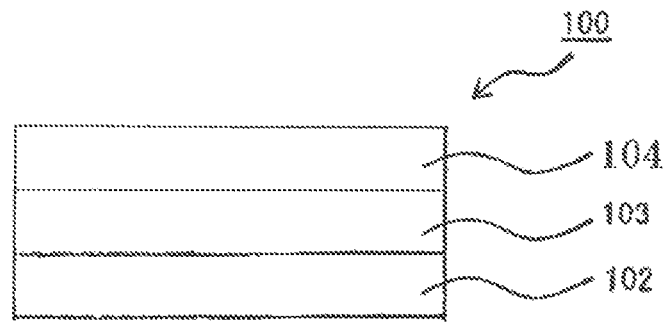
FIG. 1 illustrates an exemplary laminate containing an anisotropic light absorption film of this invention.

This invention will be detailed below. Note that, in this specification, all numerical ranges given in the form of "to", preceded and succeeded by numerals, shall be defined to contain these numerals as the lower and upper limit values.

In this specification, number-average molecular weight (Mn) may be determined typically by using HLC-8220 (from Tosoh Corporation), and TSKgel (registered trademark) Super AWM-H (from Tosoh Corporation, 6.0 mm (ID)×15.0 cm) as a column. Unless otherwise specifically noted, a 10 mol/L lithium bromide solution in NMP (N-methylpyrrolidinone) was used as the eluant.

In this specification, liquid crystal phase-isotropic phase transition temperature (Ti) may be measured by observing a liquid crystal phase on a heating stage under a polarizing microscope. More specifically, in the process of heating a sample, the temperature at which the texture changes from the liquid crystal phase to the isotropic phase is denoted as Ti.

The conventionally known polarizing plate, using iodine as the dichroic substance, has been suffering from insufficient levels of heat resistance and light resistance, due to a large sublimability of iodine. Moreover, it has not been deemed to be an achromatic polarizing element which is ideal over all visible spectrum region, due to its deep blue hue when extinguished. It has therefore been studied to use organic dyes, in place of iodine, as the dichroic substance (see JP-A-2013-109090 and JP-B2-5412225, for example). The compound of this invention has a structure in which a thienothiazolylbisazo structure and a monoazo structure are linked by a divalent linking group which interrupts the π electron conjugated system. In contrast, each of the trisazo dyes described in JP-A-2013-109090 and JP-B2-5412225 has a structure in which all azo dyes are connected through the π electron conjugated system. According to the compound of this invention having a structure in which the azo dyes are linked by a divalent linking group which interrupts the π electron conjugated system, the obtainable anisotropic light absorption film will successfully have an improved alignability, and this will successfully improve the dichroic ratio.

When the anisotropic light absorption film were formed by mixing the compound of this invention with one of, or both of yellow dye and magenta dye, in order to make the anisotropic light absorption film more blackish, the compatibility will be improved, the anisotropic light absorption film will have an improved uniformity, and thereby the anisotropic light absorption film will have an improved surface profile. What is better, the anisotropic light absorption film enjoys advantages of causing less decrease in the dichroic ratio even after stored at high temperatures, proving a high heat resistance. It was an unexpected effect that the anisotropic light absorption film containing the compound of this invention mixed with either one of; or both of yellow dye and magenta dye gained a high uniformity, and a high heat resistance.

[Compound Represented by Formula (I) or Formula (II), and Coloring Composition Containing the Compound]

The coloring composition of this invention contains one or more species of compounds represented by Formula (I) or Formula (II) below:

Formula (I)

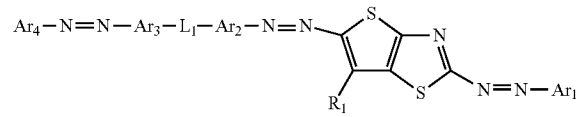

in Formula (I), $R_1$ represents a hydrogen atom or substituent, each of $Ar_1$, $Ar_2$, $Ar_3$ and $Ar_4$ independently represents an optionally substituted aromatic hydrocarbon group or optionally substituted heterocyclic group, and $L_1$ represents a divalent linking group which interrupts π electron conjugated system;

Formula (II)

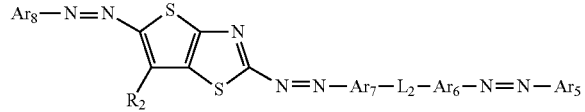

In Formula (II), $R_2$ represents a hydrogen atom or substituent, each of $Ar_5$, $Ar_6$, $Ar_7$ and $Ar_8$ independently represents an optionally substituted aromatic hydrocarbon group or optionally substituted heterocyclic group, and $L_2$ represents a divalent linking group which interrupts π electron conjugated system.

The substituents represented by $R_1$ and $R_2$ in Formula (I) and Formula (II) are preferably, but not specifically limited to, substituted or unsubstituted alkyl group, unsaturated hydrocarbon group, substituted or unsubstituted aryl group, substituted or unsubstituted heterocyclic group, halogen atom, cyano group, carboxyl group, phosphoric acid group, sulfo group, hydroxy group, substituted or unsubstituted carbamoyl group, substituted or unsubstituted sulfamoyl group, nitro group, substituted or unsubstituted alkoxy group, substituted or unsubstituted aryloxy group, substituted or unsubstituted acyl group, acyloxy group, alkoxyacyl group, acylamino group, substituted or unsubstituted sulfonyl group, amino group, or substituted amino group.

The substituted or unsubstituted alkyl group is exemplified by alkyl group preferably having 1 to 10 carbon atoms, and more preferably having 1 to 6 carbon atoms, where the substituent on the alkyl group is exemplified by alkoxy group having 1 to 6 carbon atoms, halogen atom (e.g., chlorine, bromine, iodine and fluorine atoms), aryl group having 6 to 10 carbon atoms, carboxyl group, alkoxycarbonyl group having 2 to 7 carbon atoms, and acylamino group having 1 to 6 carbon atoms. Specific examples of the substituted or unsubstituted alkyl group include methyl, ethyl, propyl, butyl, methoxymethyl, trifluoromethyl, benzyl, carboxyethyl, ethoxycarbonylmethyl and acetylaminomethyl groups.

The unsaturated hydrocarbon group is exemplified by those having 2 to 10 carbon atoms, and more specifically by vinyl group, ethynyl group, 1-cyclohexenyl group, benzylidyne group and benzylidene group.

The substituted or unsubstituted aryl group is exemplified by aryl group having 6 to 20 carbon atoms, and preferably by substituted or unsubstituted phenyl group, and substituted or unsubstituted naphthyl group, where the substituent on the aryl group is exemplified by carboxyl group, nitro group, halogen atom (e.g., chlorine, bromine, iodine and fluorine atoms), cyano group, and alkyl group having 1 to 6 carbon atoms. Specific examples of the substituted or unsubstituted aryl group include phenyl, naphthyl, paracarboxyphenyl, paranitrophenyl, 3,5-dichlorophenyl, paracyanophenyl, metafluorophenyl, and paratolyl groups.

The substituted or unsubstituted heterocyclic group is exemplified by rings composed of 1 to 3 heteroatoms selected from oxygen, nitrogen and sulfur atoms, together with carbon atom(s), where the substituent is exemplified by alkyl group having 1 to 6 carbon atoms. Specific examples of the substituted or unsubstituted heterocyclic group include pyridyl, 5-methylpyridyl, thienyl, furyl, morpholino and tetrahydrofurfuryl groups.

Specific examples of halogen atom include chlorine, bromine, iodine and fluorine atoms.

Substituent in the substituted or unsubstituted carbamoyl group is exemplified by alkyl group having 1 to 6 carbon atoms, wherein two substituents may combine to form a ring. Specific examples of the substituted or unsubstituted carbamoyl group include methylcarbamoyl, ethylcarbamoyl and morpholinocarbonyl groups.

Substituent in the substituted or unsubstituted sulfamoyl group include alkyl group having 1 to 6 carbon atoms, wherein two substituents may combine to form a ring. Specific examples of the substituted or unsubstituted sulfamoyl group include methylsulfamoyl, ethylsulfamoyl, and piperidinosulfonyl groups.

The substituted or unsubstituted alkoxy group is exemplified by substituted or unsubstituted alkoxy group having 1 to 10 carbon atoms. The substituent on the alkoxy group is exemplified by alkoxy group having 1 to 6 carbon atoms, and aryl group having 6 to 10 carbon atoms. Specific examples of the substituted or unsubstituted alkoxy group include methoxy, ethoxy, 2-methoxyethoxy and 2-phenylethoxy groups.

The substituted or unsubstituted aryloxy group is exemplified by substituted or unsubstituted aryloxy group having 6 to 20 carbon atoms, where the substituent on the aryloxy group is exemplified by alkyl group having 1 to 6 carbon atoms, and halogen atom (e.g., chlorine, bromine, iodine and fluorine atoms). Specific examples of the substituted or unsubstituted aryloxy group include phenoxy, paramethylphenoxy, parachlorophenoxy and naphthoxy groups.

The substituted or unsubstituted acyl group is preferably exemplified by substituted or unsubstituted acyl group having 1 to 20 carbon atoms, and more preferably substituted or unsubstituted acyl group having 1 to 10 carbon atoms. Specific examples of the substituent an the acyl group include halogen atom (e.g., chlorine, bromine, iodine and fluorine atoms). Specific examples of the substituted or unsubstituted acyl group include acetyl, benzoyl and trichloroacetyl groups.

The acyloxy group is preferably exemplified by acyloxy group having 1 to 10 carbon atoms. Specific examples of the acyloxy group include acetyloxy and benzoyloxy groups.

The alkoxyacyl group is preferably exemplified by alkoxyacyl group having 2 to 20 carbon atoms, and more preferably by alkoxyacyl group having 2 to 10 carbon atoms. The alkoxyacyl group is exemplified by methoxyaryl (i.e., methoxycarbonyl) and ethoxyacyl (i.e., ethoxycarbonyl) groups.

The acylamino group is preferably exemplified by acylamino group having 1 to 10 carbon atoms, and more preferably by acylamino group having 1 to 6 carbon atoms. Specific examples of the acylamino group include acetylamino group.

The substituent in the substituted or unsubstituted sulfonyl group is exemplified by alkyl group having 1 to 6 carbon atoms, or aryl group having 6 to 20 carbon atoms. Specific examples of the substituted or unsubstituted sulfonyl group include methanesulfonyl, ethanesulfonyl and benzenesulfonyl groups.

The substituent in the substituted amino group is exemplified by alkyl group having 1 to 6 carbon atoms, aryl group having 6 to 20 carbon atoms, and arylalkyl group having 7 to 20 carbon atoms. Specific examples of the substituted amino group include methylamino, dimethylamino, benzylamino, anilino and diphenylamino groups.

In Formula (I) and Formula (II), each of $R_1$ and $R_2$ preferably represents a hydrogen atom, straight-chain, branched or cyclic alkyl group having 1 to 10 carbon atoms (preferably having 1 to 6 carbon atoms, more preferably having 1 to 4 carbon atoms), aryl group having 6 to 10 carbon atoms (preferably, phenyl group or naphthyl group), halogen atom, straight-chain or branched alkoxy group having 1 to 10 (preferably 1 to 6, and more preferably 1 to 4) carbon atoms, acyl group having 1 to 10 carbon atoms, acyloxy group having 1 to 10 carbon atoms, or alkoxyacyl group having 2 to 10 carbon atoms.

In Formula (I) and Formula (II), each of $R_1$ and $R_2$ preferably represents a hydrogen atom.

In Formula (I) and Formula (II), each of $Ar_1$, $Ar_2$, $Ar_3$, $Ar_4$, $Ar_5$, $Ar_6$, $Ar_7$ and $Ar_8$ independently represents an optionally substituted aromatic hydrocarbon group, or optionally substituted heterocylic group.

The aromatic hydrocarbon group preferably has 6 to 20 carbon atoms, and more preferably having 6 to 10 carbon atoms. The aromatic hydrocarbon group is exemplified by phenyl group, phenylene group, naphthyl group and naphthylene group.

The heteroatom(s) in the heterocyclic group are 1 to 3, and preferably 1 or 2 atoms selected from oxygen atom, nitrogen atom and sulfur atom. The total number of carbon atoms and the heteroatom(s) composing the heterocycle is preferably, but not specifically limited to, 4 to 30, and more preferably 4 to 18. As the heterocyclic group, benzothiazole group is particularly preferable.

The aromatic hydrocarbon group or heterocyclic group may have a substituent Examples of the substituent which may be contained in the aromatic hydrocarbon group or hetrocyclic group include halogen atom, alkyl group, alkenyl group, alkynyl group, aralkyl group, aryl group, heterocyclic group, cyano group, hydroxy group, nitro group, carboxyl group, alkoxy group, aryloxy group, heterocyclic oxy group, acyloxy group, carbamoyloxy group, alkoxycarbonyl group, aryloxycarbonyloxy group, amino group, acylamino group, aminocarbonylamino group, alkoxycarbonylamino group, aryloxycarbonylamino group, sulfamoylamino group, alkyl- or arylsulfonylamino group, mercapto group, alkylthio group, arylthio group, heterocyclic thio group, sulfamoyl group, sulfo group, alkyl- or arylsulfinyl group, alkyl- or arylsulfonyl group, acyl group, aryloxycarbonyl group, alkoxycarbonyl group, carbamoyl group, aryl or heterocyclic azo group, imido group, phosphino group, phosphinyl group, phosphinyloxy group, phosphinylamino group, and silyl group. The substituent may further have any of these substituents. The substituent is preferably halogen atom, alkyl group, dialkylamino group, acyloxy group, or alkoxycarbonyl group.

The substituents will be detailed below.

The halogen atom is exemplified by fluorine atom, chlorine atom, bromine atom, and iodine atom.

The alkyl group is exemplified by straight-chain or branched or cyclic, substituted or unsubstituted, alkyl group, and include cycloalkyl group, bicycloalkyl group, and also tricyclo-structure having a larger number of rings. Also the alkyl group (e.g., alkyl group in alkoxy group or alkylthio group) in the substituents explained below stand on the same concept. The alkyl group is preferably a substituted or unsubstituted alkyl group having 1 to 30, more preferably 1 to 20, and even more preferably 1 to 15 carbon atoms, when summed up excluding the substituent. The cycloalkyl group is preferably a substituted or unsubstituted cycloalkyl group having 3 to 30, more preferably 3 to 20, and even more preferably 3 to 15 carbon atoms, when summed up excluding the substituent. The bicycloalkyl group is preferably a substituted or unsubstituted bicycloalkyl group having 5 to 30, more preferably 5 to 20, and even more preferably 5 to 15 bicycloalkyl group, when summed up excluding the substituent. Examples of the substituent include hydroxy group, alkoxy group, cyano group, halogen atom and ionic hydrophilic group.

The alkenyl group is exemplified by straight-chain or branched or cyclic, substituted or unsubstituted, alkenyl group, and also includes cycloalkenyl group, and bicycloalkenyl group. In more detail, the alkenyl group is preferably exemplified by substituted or unsubstituted alkenyl group having 2 to 30, more preferably 2 to 20, and even more preferably 2 to 15 carbon atoms, when summed up excluding the substituent on the alkenyl group. The cycloalkenyl group is preferably exemplified by substituted or unsubstituted cycloalkenyl group having 3 to 30, more preferably 3 to 20, and even more preferably having 3 to 15 carbon atoms when summed up excluding the substituent on the cycloalkenyl group. In other words, the cycloalkenyl group is exemplified by a monovalent group obtained by eliminating one hydrogen atom from cycloalkene having 3 to 30 carbon atoms, and, the bicycloalkenyl group is preferably exemplified by substituted or unsubstituted bicycloalkenyl group having 5 to 30, more preferably 5 to 20, and even more preferably 5 to 15 carbon atoms when summed up excluding the substituent on the bicycloalkenyl group. In other words, exemplified is a monovalent group obtained by eliminating one hydrogen atom from bicycloalkene having one double bond. Examples of the substituent include hydroxy group, alkoxy group, cyano group, halogen atom and ionic hydrophilic group.

The alkynyl group is preferably exemplified by substituted or unsubstituted alkynyl group having 2 to 30, more preferably 2 to 20, and even more preferably 2 to 15 carbon atoms when summed up excluding the substituent on the alkynyl group. Examples of the substituent include hydroxy group, alkoxy group, cyano group, halogen atom and ionic hydrophilic group.

The aralkyl group include substituted aralkyl group and unsubstituted aralkyl group. The aralkyl group is preferably a substituted or unsubstituted aralkyl group having 7 to 30, more preferably 7 to 20, and even more preferably 7 to 15 carbon atoms when summed up excluding the substituent. Examples of the substituent include hydroxy group, alkoxy group, cyano group, halogen atom and ionic hydrophilic group.

The aryl group is preferably exemplified by substituted or unsubstituted aryl group having 6 to 30, more preferably 6 to 20, and even more preferably 6 to 15 carbon atoms when summed up excluding the substituent on the aryl group. Examples of the substituent include hydroxy group, alkoxy group, cyano group, halogen atom and ionic hydrophilic group.

The heterocyclic group is preferably a monovalent group obtained by eliminating one hydrogen atom from a five- or six-membered, substituted or unsubstituted, aromatic or nonaromatic heterocyclic compound, and is more preferably a five- or six-membered, aromatic heterocyclic group having 3 to 30, more preferably 3 to 20, and even more preferably 3 to 15 carbon atoms when summed up excluding the substituent on the heterocyclic group. Examples of the substituent include hydroxy group, alkoxy group, cyano group, halogen atom and ionic hydrophilic group.

The alkoxy group is preferably exemplified by substituted or unsubstituted alkoxy group having 1 to 30, more preferably 1 to 20, and even more preferably 1 to 15 carbon atoms, when summed up excluding the substituent on the alkoxy group. Examples of the substituent include hydroxy group, alkoxy group, cyano group, halogen atom and ionic hydrophilic group.

The aryloxy group is preferably exemplified by substituted or unsubstituted aryloxy group having 6 to 30, more preferably 6 to 20, and even more preferably 6 to 15 carbon atoms, when summed up excluding the substituent on the aryloxy group. Examples of the substituent include hydroxy group, alkoxy group, cyano group, halogen atom and ionic hydrophilic group.

The heterocyclic oxy group is preferably exemplified by substituted or unsubstituted heterocyclic oxy group having 2 to 30, more preferably 2 to 20, and even more preferably 2 to 15 carbon atoms, when summed up excluding the substituent on the heterocyclic oxy group. Examples of the substituent include hydroxy group, alkoxy group, cyano group, halogen atom and ionic hydrophilic group.

The acyloxy group is preferably exemplified by formyloxy group, substituted or unsubstituted alkylcarbonyloxy group having 2 to 30 carbon atoms when summed up excluding the substituent, and more preferably substituted or unsubstituted aryl carbonyloxy group having 7 to 30, more preferably 7 to 20, and even more preferably 7 to 15 carbon atoms when summed up excluding substituent. Examples of the substituent include alkyl group, and aryl group.

The carbamoyloxy group is preferably exemplified by substituted or unsubstituted carbamoyloxy group having 1 to 30, more preferably 1 to 20, and even more preferably 1 to 15 carbon atoms, when summed up excluding the substituent on the carbamoyloxy group. Examples of the substituent include alkyl group, aryl group, and heterocyclic group.

The alkoxycarbonyloxy group is preferably exemplified by substituted or unsubstituted alkoxycarbonyloxy group having 2 to 30, more preferably 2 to 20, and even more preferably 2 to 15 carbon atoms, when summed up excluding the substituent on the alkoxycarbonyloxy group. Examples of the substituent include hydroxy group, alkoxy group, cyano group, halogen atom and ionic hydrophilic group.

The aryloxycarbonyloxy group is preferably exemplified by substituted or unsubstituted aryloxycarbonyloxy group having 7 to 30, more preferably 7 to 20, and even more preferably 7 to 15 carbon atoms when summed up excluding the substituent on the aryloxycarbonyloxy group. The substituent is exemplified by hydroxy group, alkoxy group, cyano group, halogen atom and ionic hydrophilic group.

Examples of the amino group include alkylamino group, arylamino group and heterocyclic amino group; and preferably include amino group, substituted or unsubstituted alkylamino group having 1 to 30, more preferably 1 to 20, and even more preferably 1 to 15 carbon atoms when summed up excluding the substituent and substituted or unsubstituted anilino group having 6 to 30, more preferably 6 to 20, and even more preferably 6 to 15 carbon atoms when summed up excluding the substituent. Examples of the substituent include alkyl group, aryl group, heterocyclic group, hydroxy group, alkoxy group, cyano group, halogen atom and ionic hydrophilic group.

The acylamino group is preferably exemplified by formylamino group, substituted or unsubstituted alkyl carbonylamino group having 2 to 30, more preferably 2 to 20, and even more preferably 2 to 15 carbon atoms when summed up excluding the substituent, and substituted or unsubstituted arylcarbonylamino group having 7 to 30, more preferably 7 to 20, and even more preferably 7 to 15 carbon atoms when summed up excluding the substituent. Examples of the substituent include hydroxy group, alkoxy group, cyano group, halogen atom and ionic hydrophilic group.

The aminocarbonylamino group is preferably exemplified by substituted or unsubstituted aminocarbonylamino group having 1 to 30, more preferably 1 to 20, and even more preferably having 1 to 15 carbon atoms when summed up excluding the substituent on the aminocarbonylamino group. Examples of the substituent include alkyl group, aryl group, and heterocyclic group.

The alkoxycarbonylamino group is preferably exemplified by substituted or unsubstituted alkoxycarbonylamino group having 2 to 30, more preferably 2 to 20, and even more preferably 2 to 15 carbon atoms when summed up excluding the substituent on the alkoxycarbonylamino group. Examples of the substituent include hydroxy group, alkoxy group, cyano group, halogen atom and ionic hydrophilic group.

The aryloxycarbonylamino group is preferably exemplified by substituted or unsubstituted aryloxycarbonylamino group having 7 to 30, more preferably 7 to 20, and even more preferably having 7 to 15 carbon atoms, when summed up excluding the substituent on the aryloxycarbonylamino group. Examples of the substituent include hydroxy group, alkoxy group, cyano group, halogen atom and ionic hydrophilic group.

The sulfamoylamino group is preferably exemplified by substituted or unsubstituted sulfamoylamino group having 0 to 30, more preferably 0 to 20, and even more preferably 0 to 15 carbon atoms, when summed up excluding the substituent on the sulfamoylamino group. Examples of the substituent include alkyl group, aryl group, and heterocyclic group.

The alkyl- or arylsulfonylamino group is preferably exemplified by substituted or unsubstituted alkylsulfonylamino group having 1 to 30, more preferably 1 to 20, and even more preferably 1 to 15 carbon atoms, and substituted or unsubstituted arylsulfonylamino group having 6 to 30, more preferably 6 to 20, and even more preferably 6 to 15 carbon atoms, when summed up excluding the substituent. Examples of the substituent include hydroxy group, alkoxy group, cyano group, halogen atom and ionic hydrophilic group.

The alkylthio group is preferably exemplified by substituted or unsubstituted alkylthio group having 1 to 30, more preferably 1 to 20, and even more preferably 1 to 15 carbon atoms, when summed up excluding the substituent on the alkylthio group. Examples of the substituent include hydroxy group, alkoxy group, cyano group, halogen atom and ionic hydrophilic group.

The arylthio group is preferably exemplified by substituted or unsubstituted arylthio group having 6 to 30, more preferably 6 to 20, and even more preferably 6 to 15 carbon atoms, when summed up excluding the substituent on the arylthio group. Examples of the substituent include hydroxy group, alkoxy group, cyano group, halogen atom and ionic hydrophilic group.

The heterocyclic thio group is preferably exemplified by substituted or unsubstituted heterocyclic thio group having 2 to 30, more preferably 2 to 20, and even more preferably 2 to 15 carbon atoms, when summed up excluding the substituent on the heterocyclic thio group. Examples of the substituent include hydroxy group, alkoxy group, cyano group, halogen atom and ionic hydrophilic group.

The sulfamoyl group is preferably exemplified by substituted or unsubstituted sulfamoyl group having 0 to 30, more preferably 0 to 20, and even more preferably 0 to 15 carbon atoms, when summed up excluding the substituent on the sulfamoyl group. Examples of the substituent include alkyl group, aryl group, and heterocyclic group.

The alkyl- or arylsulfinyl group is preferably exemplified by substituted or unsubstituted alkylsulfinyl group having 1 to 30, more preferably 1 to 20, and even more preferably 1 to 15 carbon atoms, when summed up excluding the substituent, and substituted or unsubstituted arylsulfinyl group having 6 to 30, more preferably 6 to 20, and even more preferably 6 to 15 carbon atoms, when summed up excluding the substituent. Examples of the substituent include hydroxy group, alkoxy group, cyano group, halogen atom and ionic hydrophilic group.

The alkyl- or arylsulfonyl group is preferably exemplified by substituted or unsubstituted alkylsulfonyl group having 1 to 30, more preferably 1 to 20, and even more preferably 1 to 15 carbon atoms, when summed up excluding the substituent, and substituted or unsubstituted arylsulfonyl group having 6 to 30, more preferably 6 to 20, and even more preferably 6 to 15 carbon atoms when summed up excluding the substituent. Examples of the substituent include hydroxy group, alkoxy group, cyano group, halogen atom and ionic hydrophilic group.

The acyl group is preferably exemplified by formyl group; substituted or unsubstituted alkyl carbonyl group having 2 to 30, more preferably 2 to 20, and even more preferably 2 to 15 carbon atoms when summed up excluding the substituent; substituted or unsubstituted arylcarbonyl group having 7 to 30, more preferably 7 to 20, and even more preferably 7 to 15 carbon atoms when summed up excluding the substituent; and substituted or unsubstituted heterocyclic carbonyl group having 2 to 30, more preferably 2 to 20, and even more preferably 2 to 15 carbon atoms when summed up excluding the substituent, wherein the heterocycle is bound to the carbonyl group at carbon atom. Examples of the substituent include alkyl group, aryl group, and heterocyclic group.

The aryloxycarbonyl group is preferably exemplified by substituted or unsubstituted aryloxycarbonyl group having 7 to 30, more preferably 7 to 20, and even more preferably 7 to 15 carbon atoms, when summed up excluding the substituent on the aryloxycarbonyl group. Examples of the substituent include hydroxy group, alkoxy group, cyano group, halogen atom and ionic hydrophilic group.

The alkoxycarbonyl group is preferably exemplified by substituted or unsubstituted alkoxycarbonyl group having 2 to 30, more preferably 2 to 20, and even more preferably 2 to 15 carbon atoms, when summed up excluding the substituent on the alkoxycarbonyl group. Examples of the substituent include hydroxy group, alkoxy group, cyano group, halogen atom and ionic hydrophilic group.

The carbamoyl group is preferably exemplified by substituted or unsubstituted carbamoyl group having 1 to 30, more preferably 1 to 20, and even more preferably 1 to 15 carbon atoms, when summed up excluding the substituent on the carbamoyl group. Examples of the substituent include alkyl group, aryl group, and heterocyclic group.

The aryl or heterocyclic azo group is preferably exemplified by substituted or unsubstituted arylazo group having 6 to 30, more preferably 6 to 20, and even more preferably 6 to 15 carbon atoms when summed up excluding the substituent; and substituted or unsubstituted hetrocyclic azo group having 3 to 30, more preferably 3 to 20, and even more preferably 3 to 15 carbon atoms when summed up excluding the substituent. Examples of the substituent include hydroxy group, alkoxy group, cyano group, halogen atom and ionic hydrophilic group.

The imido group is preferably exemplified by substituted or unsubstituted imido group having 0 to 30, more preferably 0 to 20, and even more preferably 0 to 15 carbon atoms when summed up excluding the substituent on the imido group. Examples of the substituent include alkyl group, aryl group, and heterocyclic group.

The phosphino group is preferably exemplified by substituted or unsubstituted phosphino group having 0 to 30, more preferably 0 to 20, and even more preferably 0 to 15 carbon atoms when summed up excluding the substituent.

The phosphinyl group is preferably exemplified by substituted or unsubstituted phosphinyl group having 0 to 30, more preferably 0 to 20, and even more preferably 0 to 15 carbon atoms when summed up excluding the substituent. Examples of the substituent include alkyl group, aryl group, and heterocyclic group.

The phosphinyloxy group is preferably exemplified by substituted or unsubstituted phosphinyloxy group having 0 to 30, more preferably 0 to 20, and even more preferably 0 to 15 carbon atoms when summed up excluding the substituent. Examples of the substituent include alkyl group, aryl group, and heterocyclic group.

The phosphinylamino group is preferably exemplified by substituted or unsubstituted phosphinylamino group having 0 to 30, more preferably 0 to 20, and even more preferably 0 to 15 carbon atoms when summed up excluding the substituent. Examples of the substituent include alkyl group, aryl group, and heterocyclic group.

The silyl group is preferably exemplified by substituted or unsubstituted silyl group having 0 to 30, more preferably 0 to 20, and even more preferably 0 to 15 carbon atoms when summed up excluding the substituent. Examples of the substituent include alkyl group, aryl group and heterocyclic group.

The ionic hydrophilic group is preferably a sulfo group, carboxyl group, or phosphono group, and is more preferably a sulfo group or carboxyl group.

Each hydrophilic group may have a free acid form or salt form. Counter cation which forms the salt is preferably exemplified by alkali metal ion (lithium ion, sodium ion, potassium ion), alkali earth metal ion (magnesium ion, calcium ion), and quaternary ammonium ion (ammonium ion, tetraalkylammonium ion, tetraarylammonium ion, etc.), more preferably lithium ion, sodium ion, potassium ion and ammonium ion, and most preferably lithium ion.

In Formulae (I) and (II), each of $L_1$ and $L_2$ represents a divalent linking group which interrupts the π electron conjugated system. The divalent linking group which interrupts the π electron conjugated system is preferably a group other than the group which contains a double bond in the principal chain, and capable of forming a π electron conjugated system using such double bond when neighbored with other double bond (e.g., —N=N—, —CH=N—, —CH=CH—).

In Formulae (I) and (II), each of $L_1$ and $L_2$ preferably represents —O(C=O)—, —(C=O)O—, —O—, —CH$_2$—, or combination thereof.

The divalent linking group which interrupts the π electron conjugated system will suffice if it contains at least one divalent linking group which interrupts the π electron conjugated system (e.g., —O(C=O)—, —(C=O)O—, —O—, —CH$_2$, or combination of them) in the principal chain. In other words, the divalent linking group which interrupts the π electron conjugated system may be a group obtained by combining at least one divalent linking group which interrupts the π electron conjugated system, with a group having a double bond in the principal chain and capable of forming an electron conjugated system using such double bond when neighbored with other double bond (e.g., —N=N—, —CH=N—, —CH=CH—). Specific examples include —C(=O)—CH$_2$CH$_2$—, —C(O)—O—CH$_2$—, —O—C(=O)—O—, —O—C(O)—NH—, —CH=CHO—CH$_2$—, and —O—CH$_2$—.

The compound represented by Formula (I) or Formula (II) is preferably any of the compounds represented by Formula (IA) or (IIA) below:

Formula (IA)

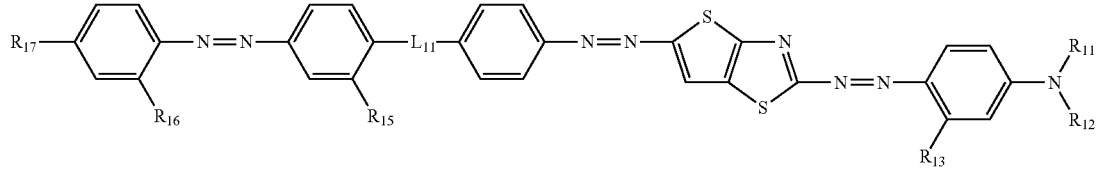

in Formula (IA), each of $R_{11}$ and $R_{12}$ independently represents an alkyl group having 1 to 6 carbon atoms or polymerizable group, each of $R_{13}$, $R_{14}$, $R_{15}$ and $R_{16}$ independently represents a hydrogen atom, alkyl group having 1 to 6 carbon atoms or alkoxy group having 1 to 6 carbon atoms, $R_{17}$ represents an alkyl group having 1 to 6 carbon atoms, alkoxy group having 1 to 6 carbon atoms, alkoxycarbonyl group having 2 to 6 carbon atoms, acyl group having 1 to 6 carbon atoms, or polymerizable group, and $L_{11}$ represents —O(C=O)—, —CH$_2$CH$_2$—, —CH$_2$O—, —(C=O)O—, or —O—;

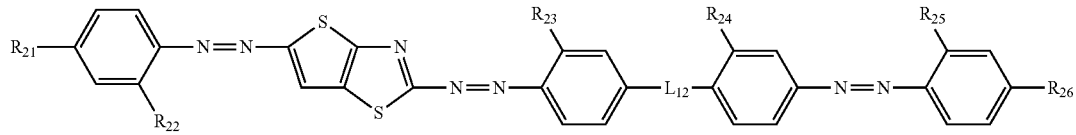

Formula (IIA)

in Formula (IIA), $R_{21}$ represents —$N(R_{31})(R_{32})$, alkyl group having 1 to 6 carbon atoms, alkoxycarbonyl group having 2 to 6 carbon atoms, or polymerizable group, each of $R_{22}$, $R_{23}$, $R_{24}$ and $R_{25}$ independently represents a hydrogen atom, alkyl group having 1 to 6 carbon atoms or alkoxy group having 1 to 6 carbon atoms, $R_{26}$ represents an alkyl group having 1 to 6 carbon atoms, alkoxy group having 1 to 6 carbon atoms, alkoxycarbonyl group having 2 to 6 carbon atoms, or —$N(R_{41})(R_{42})$, and $L_{12}$ represents —O(C=O)—, —$CH_2CH_2$—, —$OCH_2$—, or —(C=O)O—, where each of $R_{31}$ and $R_{32}$ independently represents an alkyl group having 1 to 6 carbon atoms or polymerizable group, and each of $R_{41}$ and $R_{42}$ independently represents an alkyl group having 1 to 6 carbon atoms.

The polymerizable group is preferably, for example, an addition-polymerizable functional group which is exemplified by ethylenic unsaturated linking group. The ethylenic unsaturated linking group is preferably stylyl group, (meth)acryloyl group and allyl group, wherein (meth)acryloyl group is more preferable. Also preferable is an alkylene group having the above-described ethylenic unsaturated linking group bound to the terminal.

Specific examples of the compounds represented by Formula (I) and Formula (II), and their wavelength of maximum absorbance values are listed below Method of measuring the wavelength of maximum absorbance will be described later.

Wavelength of maximum absorbance [λmax (nm)] (solvent for measurement N-methylpyrrolidone)

| No. | λmax (nm) |
|-----|-----------|
| 1   | 632       |
| 2   | 632       |
| 3   | 622       |
| 4   | 614       |
| 5   | 620       |
| 6   | 612       |
| 7   | 632       |
| 8   | 633       |
| 9   | 630       |

TABLE 1

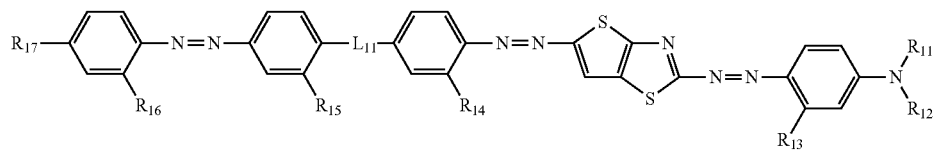

| No. | $R_{11}$ | $R_{12}$ | $R_{13}$ | $R_{14}$ | $R_{15}$ | $R_{16}$ | $R_{17}$ | $L_{11}$* |
|-----|----------|----------|----------|----------|----------|----------|----------|-----------|
| 1 | $C_2H_5$ | $C_2H_5$ | H | H | H | H | n-$C_4H_9$ | —O(C=O)— |
| 2 | $C_2H_5$ | $C_2H_5$ | H | H | H | $CH_3$ | n-$C_3H_7$ | —O(C=O)— |
| 3 | $C_2H_5$ | $C_2H_5$ | $CH_3$ | H | H | H | $OC_2H_5$ | —$CH_2CH_2$— |
| 4 | $C_2H_5$ | $C_2H_5$ | H | H | $CH_3$ | H | —$CO_2C_2H_5$ | —$CH_2O$— |
| 5 | $C_2H_5$ | $C_2H_5$ | H | $CH_3$ | H | H | O—n-$C_4H_9$ | —(C=O)O— |
| 6 | $CH_3$ | n-$C_3H_7$ | $OCH_3$ | H | H | H | $COC_4H_9$ | —O— |
| 7 | $C_2H_5$ | n-$C_4H_9$ | H | H | H | $CH_3$ | n-$C_3H_7$ | —O(C=O)— |
| 8 | $C_2H_5$ | $CH_2CH_2O(CO)CH=CH_2$ | H | H | H | H | n-$C_4H_9$ | —O(C=O)— |
| 9 | $C_2H_5$ | $CH_2CH_2O(CO)CH=CH_2$ | H | H | H | $CH_3$ | $OCH_2CH_2O(CO)CH=CH_2$ | —O(C=O)— |

*Linking moiety given from the left to right.

TABLE 2

| No. | $R_{21}$ | $R_{22}$ | $R_{23}$ | $R_{24}$ | $R_{25}$ | $R_{26}$ | $L_{12}$* |
|---|---|---|---|---|---|---|---|
| 10 | $-N(C_2H_5)_2$ | H | H | H | H | $n-C_4H_9$ | $-O(C=O)-$ |
| 11 | $-N(C_2H_5)_2$ | H | H | H | $CH_3$ | $n-C_3H_7$ | $-O(C=O)-$ |
| 12 | $-N(C_2H_5)_2$ | $CH_3$ | $CH_3$ | H | H | $OC_2H_5$ | $-CH_2CH_2-$ |
| 13 | $-N(C_2H_5)_2$ | $C_2H_5$ | H | $CH_3$ | H | $CO_2C_2H_5$ | $-OCH_2-$ |
| 14 | $n-C_4H_9$ | H | H | H | H | $-N(C_2H_5)_2$ | $-O(C=O)-$ |
| 15 | $CO_2-n-C_4H_9$ | H | $OCH_3$ | H | H | $-N(C_2H_5)_2$ | $-O(C=O)-$ |
| 16 | $CO_2(CH_2)_4O(CO)CH=CH_2$ | H | H | H | H | $-N(C_2H_5)_2$ | $-O(C=O)-$ |
| 17 | $-N(C_2H_5)CH_2CH_2O(CO)CH=CH_2$ | H | H | H | H | $-N(C_2H_5)_2$ | $-(C=O)O-$ |

*Linking moiety given from the left to right.

Wavelength of maximum absorbance [λmax (nm)] (solvent for measurement: N-methylpyrrolidone)

| No. | λmax (nm) |
|---|---|
| 10 | 610 |
| 11 | 602 |
| 12 | 618 |
| 13 | 620 |
| 14 | 565 |
| 15 | 540 |
| 16 | 540 |
| 17 | 605 |

The compound represented by Formula (I) may be synthesized according to a method described later in Exemplary Synthesis 1, and the compound represented by Formula (II) may be synthesized according to a method described later in Exemplary Synthesis 2.

According to Exemplary Synthesis 1, in Step 1, paraaminobenzoic acid is allowed to react with a diazotizing agent to produce a diazonium compound. Next, the diazonium compound is allowed to react with 2-aminothiophene to produce a monoazo compound. In Step 2, the monoazo compound is allowed to react with sodium thiocyanate to produce a monoazo compound having an amino group-containing thienothiazole ring. In Step 3, the monoazo compound is allowed to react with a diazotizing agent to produce a diazonium compound, and then the diazonium compound is allowed to react with diethylaniline to produce a bisazo compound. In Step 4, the bisazo compound is allowed to react with 4-butylphenylazophenol for esterification, to thereby produce the target compound represented by Formula (I).

According to Exemplary Synthesis 2, in Step 1, 4-butylaniline is allowed to react with a diazotizing agent to produce a diazonium compound. Next, the diazonium compound is allowed react with 2-aminothiophene to produce a monoazo compound. In Step 2, the monoazo compound is allowed to react with sodium thiocyanate, to produce a monoazo compound having an amino group-containing thienothiazole ring. In Step 3, the monoazo compound is allowed to react with a diazotizing agent to produce a diazonium compound, and then the diazonium compound is allowed to react with phenol to produce a bisazo compound. In Step 4, the bisazo compound is allowed to react with 4-(4-diethylamino-phenylazo)benzoic acid for esterification, to thereby produce the target compound represented by Formula (II).

The diazotizing agent used in the synthesis is preferably any of sodium nitrite, isopentyl nitrite and nitrosylsulfuric acid. Sodium nitrite and nitrosylsulfuric acid are most preferable.

Amount of consumption of the diazotizing agent is not specifically limited so long as the reaction can proceed, and is preferably 0.5 to 2-fold, more preferably 0.7 to 1.5-fold, and even more preferably 1.0 to 1.5-fold ratio by mole relative to the amount of consumption of the source compound.

Solvent usable herein is preferably an acid capable of slightly, not to say completely, dissolving the source compound, but preferably an acid capable of completely dissolving it. As the acid, usable are inorganic acid (also referred to as mineral acid) and organic acid. The inorganic acid is exemplified by hydrochloric acid, phosphoric acid and sulfuric acid. The organic acid is exemplified by formic acid, acetic acid, propionic acid and methanesulfonic acid. Acetic acid, propionic acid and methanesulfonic acid are preferable, and acetic acid and methanesulfonic acid are even more preferable. These acids may be used independently or as a mixed acid. The mixed acid is exemplified by phosphoric acid/acetic acid, sulfuric acid/acetic acid, methanesulfonic acid/acetic acid, methanesulfonic acid/propionic acid, and acetic acid/propionic acid, more preferably exemplified by sulfuric acid/acetic acid, methanesulfonic acid/acetic acid, and methanesulfonic acid/propionic acid, and even more preferably exemplified by sulfuric acid/acetic acid. The mixed acid may contain three or more species.

A preferable combination of the azotizing agent and the solvent is a combination of sodium nitrite and hydrochloric acid.

Reaction time over which the derivation towards the diazonium salt proceeds is preferably 0.3 to 10 hours, more preferably 0.5 to 5 hours, and even more preferably 0.5 to 3 hours. Temperature at which the derivation towards the diazonium salt proceeds is preferably 20° C. or below, more preferably 10° C. or below, and even more preferably 5° C. or below.

Coupling reaction of the diazonium salt with other compound may be allowed to proceed by adding a solution containing the diazonium salt, to a solution prepared by dissolving the other compound into a suitable solvent (e.g., alcohol such as methanol).

Amount of consumption of the other compound is not specifically limited so long as the reaction can proceed, and is preferably 0.5 to 2-fold, more preferably 0.7 to 1.5-fold, and even more preferably 0.8 to 1.2-fold ratio by mole relative to the amount of the diazonium salt.

Reaction time for the coupling reaction is preferably 0.3 to 10 hours, more preferably 0.5 to 5 hours, and even more preferably 0.5 to 3 hours.

Reaction temperature for the coupling reaction is preferably 5° C. to 40° C., and more preferably 10° C. to room temperature.

Content of the compound represented by Formula (I) or Formula (II) in the coloring composition of this invention is preferably 10 to 100% by mass, and more preferably 20 to 100% by mass, relative to the solid content of the coloring composition. Only a single species of the compound represented by Formula (I) or Formula (II) may be used, or two or more species thereof may be used in combination. When two or more species are used in combination, the total content preferably falls in the above-described ranges.

[Other Coloring Compound]

The coloring composition of this invention may further contain one or more species of coloring compound other than the compound represented by Formula (I) or Formula (II). The coloring compound other than the compound represented by Formula (I) or Formula (II) is exemplified by azo dyes, cyanine dyes, azo-metal complex, phthalocyanine dyes, pyrylium dyes, perylene dyes, anthraquinone dyes, squarylium dyes, quinoline dyes, triphenylmethane dyes, and triallylmethane dyes. Among them, compounds having wavelength of maximum absorbance values of 400 to 600 nm are preferably used as the coloring compound other than compound represented by Formula (I) or Formula (II).

The one of more species of the coloring compound other than the compound represented by Formula (I) or Formula (II) is preferably any of compounds represented by Formula (III) or Formula (IV) below:

Formula (III)

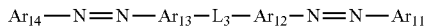

$Ar_{14}-N=N-Ar_{13}-L_3-Ar_{12}-N=N-Ar_{11}$ in Formula (III), each of $Ar_{11}$, $Ar_{12}$, $Ar_{13}$ and $Ar_{14}$ independently represents an optionally substituted aromatic hydrocarbon group or optionally substituted heterocyclic group, and $L_3$ represents a divalent linking group.

Formula (IV)

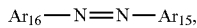

$Ar_{16}-N=N-Ar_{15}$, in Formula (IV), each of $Ar_{15}$ and $Ar_{16}$ independently represents an optionally substituted aromatic hydrocarbon group or optionally substituted heterocyclic group.

Each of $Ar_{11}$, $Ar_{12}$, $Ar_{13}$, $Ar_{14}$, $Ar_{15}$ and $Ar_{16}$ is preferably an optionally substituted phenyl group, optionally substituted naphthyl group, or optionally substituted heterocyclic group. These substituents may further have substituents. The substituent is preferably a group introduced for the purpose of enhancing solubility of the azo compound or nematic liquid crystallinity, an electron donating or electron attractive group introduced for the purpose of controlling the hue of the coloring compound as a dye, or a group having a polymerizable group introduced for the purpose of fixing the alignment. Examples of the substituent include alkyl group (preferably having 1 to 20, more preferably 1 to 12, and particularly 1 to 8 carbon atoms, exemplified by methyl group, ethyl group, isopropyl group, tert-butyl group, n-octyl group, n-decyl group, n-hexadecyl group, cyclopropyl group, cyclopentyl group and cyclohexyl group); alkenyl group (preferably having 2 to 20, more preferably 2 to 12, and particularly 2 to 8 carbon atoms, exemplified by vinyl group, aryl group, 2-butenyl group and 3-pentenyl group); alkynyl group (preferably having 2 to 20, more preferably 2 to 12, particularly 2 to 8 carbon atoms, exemplified by propargyl group and 3-pentynyl group); aryl group (preferably having 6 to 30, more preferably 6 to 20, and particularly 6 to 12 carbon atoms, exemplified by phenyl group, 2,6-diethylphenyl group, 3,5-ditrifluoromethylphenyl group, naphthyl group and biphenyl group); substituted or unsubstituted amino group (preferably having 0 to 20, more preferably 0 to 10, and particularly 0 to 6 carbon atoms, exemplified by unsubstituted amino group, methylamino group, dimethylamino group, diethylamino group and anilino group); alkoxy group (preferably having 1 to 20, more preferably 1 to 10, and particularly 1 to 6 carbon atoms, exemplified by methoxy group, ethoxy group and butoxy group); oxycarbonyl group (preferably having 2 to 20, more preferably 2 to 15, and particularly 2 to 10 carbon atoms, exemplified by methoxycarbonyl group, ethoxycarbonyl group and phenoxycarbonyl group); acyloxy group (preferably having 2 to 20, more preferably 2 to 10, and particularly 2 to 6 carbon atoms, exemplified by acetoxy group and benzoyloxy group); acylamino group (preferably having 2 to 20, more preferably 2 to 10, and particularly 2 to 6 carbon atoms, exemplified by acetylamino group and benzoylamino group); alkoxycarbonylamino group (preferably having 2 to 20, more preferably 2 to 10, and particularly 2 to 6 carbon atoms, exemplified by methoxycarbonylamino group); aryloxycarbonylamino group (preferably having 7 to 20, more preferably 7 to 16, and particularly 7 to 12 carbon atoms, exemplified by phenyloxycarbonylamino group); sulfonylamino group (preferably having 1 to 20, more preferably 1 to 10, and particularly having 1 to 6 carbon atoms, exemplified by methanesulfonylamino group and benzenesulfonylamino group); sulfamoyl group (preferably having 0 to 20, more preferably 0 to 10, and particularly 0 to 6 carbon atoms, exemplified by sulfamoyl group, methylsulfamoyl group, dimethylsulfamoyl group and phenylsulfamoyl group); carbamoyl group (preferably having 1 to 20, more preferably 1 to 10, and particularly 1 to 6 carbon atoms, exemplified by unsubstituted carbamoyl group, methylcarbamoyl group, diethylcarbamoyl group and phenylcarbamoyl group); alkylthio group (preferably having 1 to 20, more preferably 1 to 10, and particularly 1 to 6 carbon atoms, exemplified by methylthio group and ethylthio group); arylthio group (preferably having 6 to 20, more preferably 6 to 16, and particularly 6 to 12 carbon atoms, exemplified by phenylthio group); sulfonyl group (preferably having 1 to 20, more preferably 1 to 10, and particularly 1 to 6 carbon atoms, exemplified by mesyl group and tosyl group); sulfinyl group (preferably having 1 to 20, more preferably 1 to 10, and particularly 1 to 6 carbon atoms, exemplified by methanesulfinyl group and benzenesulfinyl group); ureido group (preferably having 1 to 20, more preferably 1 to 10, and particularly 1 to 6 carbon atoms, exemplified by unsubstituted ureido group, methylureido group and phenylureido group); phosphoric acid amide group (preferably having 1 to 20, more preferably 1 to 10, and particularly 1 to 6 carbon atoms, exemplified by diethylphosphoric acid amide group and phenylphosphoric acid amide group); hydroxy group; mercapto group; halogen atom (e.g., fluorine atom, chlorine atom, bromine atom and iodine atom); cyano group; intro group; hydroxamic acid group; sulfino group; hydrazino group; imino group; azo group; heterocyclic group (preferably having 1 to 30, and more preferably 1 to 12 carbon atoms, which is typically heterocyclic group having heteroatom(s) such as nitrogen atom, oxygen atom and sulfur atom, and is exemplified by imidazolyl group, pyridyl group, quinolyl group, furyl group, piperidyl group, morpholino group, benzoxazolyl group, benzimidazolyl group and benzthiazolyl group); and silyl group (preferably having 3 to 40, more preferably 3 to 30, and particularly 3 to 24 carbon atoms, exemplified by trimethylsilyl group and triphenylsilyl group). Each of these substituents may further be substituted by any of these substituents. When there are two or more substituents, they may be same or different. If possible, the substituents may combine to form a ring.

The substituent is preferably an optionally substituted alkyl group, optionally substituted alkenyl group, optionally substituted alkynyl group, optionally substituted aryl group, optionally substituted alkoxy group, optionally substituted oxycarbonyl group, optionally substituted acyloxy group, optionally substituted acylamino group, optionally substituted amino group, optionally substituted alkoxycarbonylamino group, optionally substituted sulfonylamino group, optionally substituted sulfamoyl group, optionally substituted carbamoyl group, optionally substituted alkylthio group, optionally substituted sulfonyl group, optionally substituted ureido group, nitro group, hydroxy group, cyano group, imino group, azo group, or halogen atom, and is particularly preferably an optionally substituted alkyl group, optionally substituted alkenyl group, optionally substituted aryl group, optionally substituted alkoxy group, optionally substituted oxycarbonyl group, optionally substituted acyloxy group, nitro group, imino group, or azo group.

The aromatic heterocyclic group is preferably monocyclic or bicyclic heterocycle-derived group. Atom other than the carbon atom composing aromatic heterocyclic group is exemplified by nitrogen atom, sulfur atom and oxygen atom. When the aromatic heterocyclic group has a plurality of ring-composing atoms other than carbon atom, they may be same or different. Specific examples of the aromatic heterocyclic group include pyridyl group, quinolyl group, thiophenyl group, thiazolyl group, benzothiazolyl group, thiadiazolyl group, quinolonyl group, naphthalimidoyl group, thienothiaolyl group, and heterocyle-derived group represented by the formula below.

$L_3$ represents a divalent linking group. Specific examples of the divalent linking group include groups selected from the group G of structural units below, or groups obtained by combining these structural units.

Group G of Structural Units

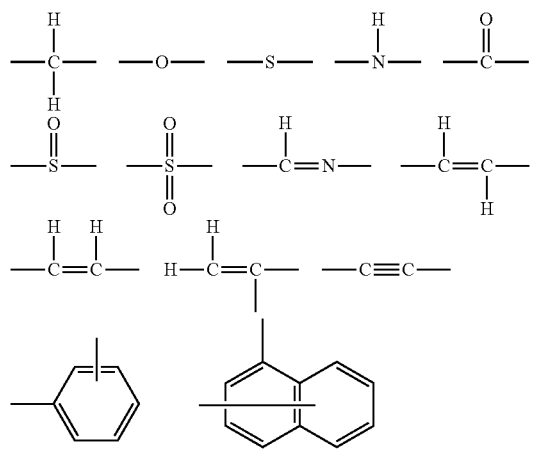

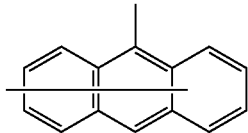

$L_3$ preferably represents a single bond, or, a divalent organic coupling group composed of 1 to 50 carbon atoms, 0 to 8 nitrogen atoms, 0 to 25 oxygen atoms, 1 to 100 hydrogen atoms, and 0 to 10 sulfur atoms; more preferably represents a single bond, or, a divalent organic coupling group composed of 1 to 30 carbon atoms, to 6 nitrogen atoms, 0 to 15 oxygen atoms, 1 to 50 hydrogen atoms, and 0 to 7 sulfur atoms; and particularly represents a single bond, or, a divalent organic coupling group composed of 1 to 10 carbon atoms, 0 to 5 nitrogen atoms, 0 to 10 oxygen atoms, 1 to 30 hydrogen atoms, and 0 to 5 sulfur atoms.

$L_3$ preferably represents an alkylene group, ether group, ester group, ethylene group, or phenylene group.

Content of the other coloring compound in the coloring composition of this invention is preferably 5 to 50% by mass, and more preferably 10 to 40% by mass, relative to the solid content of the coloring composition. Only a single species of the other coloring compound may be used independently, or two or more species thereof may be used in combination. When two or more species are used in combination, the total content preferably falls within the above-descried ranges.

[Thermotropic Liquid Crystalline Polymer]

The coloring composition of this invention may further contain one or more species of thermotropic liquid crystalline polymer.

The thermotropic liquid crystalline polymer usable in this invention preferably has, from the viewpoint of suitability to ripening under heating and heat resistance, a liquid crystal phase-isotropic phase transition temperature of 200° C. or higher, more preferably 250° C. or higher, and particularly 300° C. or higher. Although the thermotropic liquid crystalline polymer is not specifically limited regarding the molecular weight, it preferably has a number-average molecular weight Mn of 2,000 to 200,000, and more preferably 3,000 to 50,000, when given in the form of main-chain polymer liquid crystal, typically from the viewpoints of solubility when prepared in the form of coating liquid, and of compatibility with the compound of this invention represented by Formula (I) or Formula (II). When given in the form of side-chain polymer liquid crystal, it preferably has a number-average molecular weight Mn of 1,000 to 200,000, and more preferably 1,500 to 10,000.

Although both of the thermotropic liquid crystalline polymers in the form of main-chain polymer and in the form of side-chain polymer are usable, the side-chain polymer is more preferable from the viewpoint of compatibility with the dichroic dye. Again from the viewpoint of compatibility, the thermotropic liquid crystalline polymer preferably has a structural similarity with the dichroic dye to be used in combination. In this invention, it is preferable to use a liquid crystalline polymer having an azo group in the molecule thereof. Moreover, by using a liquid crystalline polymer having absorption transition in the visible light region, the liquid crystalline polymer also contributes to increase the dichroic ratio of the anisotropic light absorption film, making it possible to thin the film.

Preferable examples of the main-chain liquid crystalline polymer include polyester, polyurethane, polyester amide, polyamide, polycarbonate, polyazomethylene, polyether and polythiol. Polyester is particularly preferable. The main-chain liquid crystalline polymer is categorized into rigid-type ones composed of aromatic rings only, and semi-flexible-type ones containing a flexible chain. From the viewpoint of adequate phase transition temperature and orderliness of alignment, the semi-flexible-type ones are preferable.

Specific examples of the main-chain liquid crystalline polymer include those described in paragraphs [0023] to [0035] of JP-B2-5566178, the contents of which are incorporated into this specification.

Preferable examples of the side-chain liquid crystalline polymer include polyacrylate, polymethacrylate, polyacrylamide, polyethylene oxide, polyethyleneimine, polystyrene and polysiloxane. Polyacrylate and polymethacrylate are particularly preferable.

The side-chain liquid crystalline polymer is categorized into terminal bonding-type ones in which a mesogen is bound at the terminal thereof via a spacer or a single bond to the principal chain, and side bonding-type ones in which a mesogen is bound on the side portion thereof via a spacer to the principal chain.

Specific examples of the side-chain liquid crystalline polymer include those described in paragraphs [0037] to [0055] of JP-B2-5566178, the contents of which are incorporated into this specification.

The thermotropic liquid crystalline polymer is preferably a polymer having at least a repeating unit represented by any one of Formulae (IX-a), (IX-b) and (IX-c) below:

represents an integer of 0 to 2; m2 represents an integer of 1 or 2; each of $R^a$, $R^b$ and $R^c$ independently represents a substituent; and each of x, y and z independently represents an integer of 0 to 4.

Content of the thermotropic liquid crystalline polymer in the coloring composition of this invention is preferably 10 to 70% by mass, and more preferably 20 to 60% by mass, relative to the solid content of the coloring composition. Only a single species of the thermotropic liquid crystalline polymer may be used, or two or more species thereof may be used in combination. When two or more species are used in combination, the total content preferably falls within the above-described ranges.

[Horizontal Alignment Agent]

The coloring composition of this invention may further contain a horizontal alignment agent.

The horizontal alignment agent is a compound which prompts the compound of this invention represented by Formula (I) or Formula (II) to align substantially in a horizontal direction. The horizontal alignment agent is preferably at least one species of the compound represented by any of Formulae (1) to (3) below. By adding the horizontal alignment agent the anisotropic light absorption film may be prevented from causing alignment failure and irregularity at the interface with air, and may further be improved in uniformity of the surface profile. Now, the "horizontal alignment" means that the long axis direction of the dichroic dye lies in parallel with the horizontal plane of the aniso-

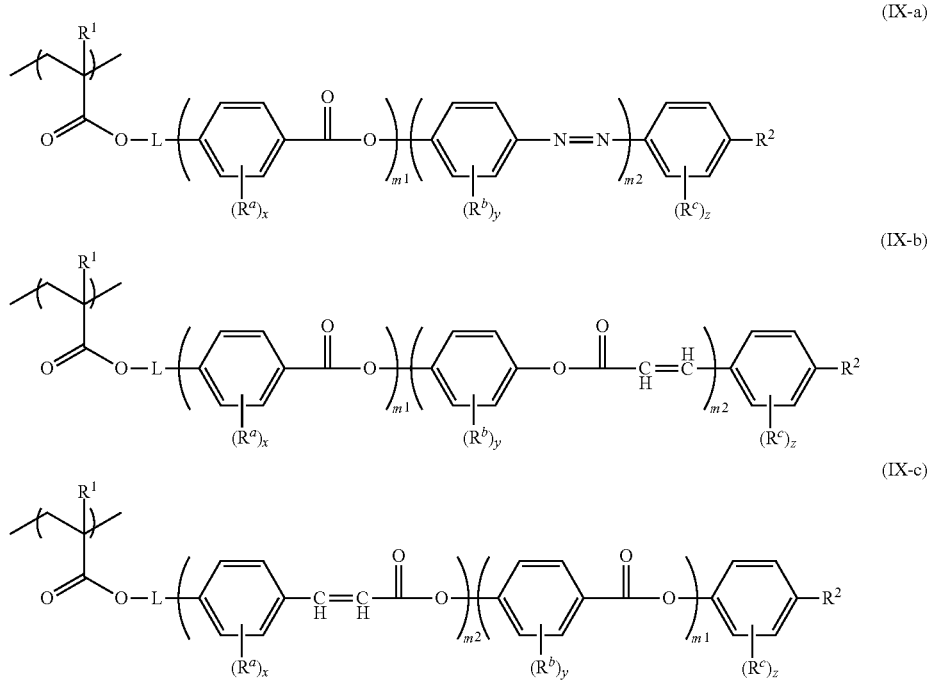

in Formulae (IX-a), (IX-b) and (IX-c), $R^1$ represents a hydrogen atom or methyl group; L represents a single bond, —$(CH_2)_{x1}O$—, or —$(CH_2CH_2O)_{y1}$—, x1 represents an integer of 2 to 10, y1 represents an integer of 1 to 5, $R^2$ represents a hydrogen atom, alkyl group having 1 to 10 carbon atoms, alkoxy group having 1 to 9 carbon atoms, cyano group, or optionally substituted amino group; m1 tropic light absorption film, without claiming perfect parallelism, instead meaning in this specification that the long axis direction and the horizontal plane make an inclination angle of smaller than 10 degrees. The inclination angle is preferably 5 degrees or smaller, and more preferably 3 degrees or smaller, even more preferably 2 degrees or smaller, and yet more preferably 1 degree or smaller.

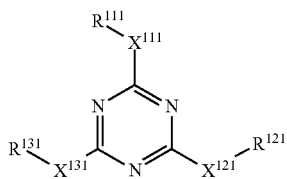

Formula (1)

In the formula, each of $R^{111}$, $R^{121}$ and $R^{131}$ independently represents a hydrogen atom or substituent, and each of $X^{111}$, $X^{121}$ and $X^{131}$ independently represents a single bond or divalent linking group.

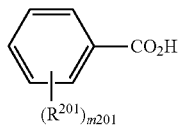

Formula (2)

In the formula, $R^{201}$ represents a substituent, and m201 represents an integer of 0 to 5. If m201 represents an integer of 2 or larger, the plurality of $(R^{201})$s may be same or different

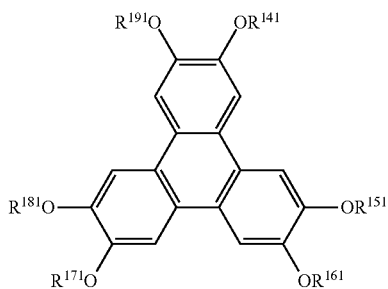

Formula (3)

In the formula, each of $R^{141}$, $R^{151}$, $R^{161}$, $R^{171}$, $R^{181}$ and $R^{191}$ independently represents a hydrogen atom or substituent.

The compound represented by Formula (1) will be explained.

The substituent independently represented by $R^{111}$, $R^{121}$ and $R^{131}$ is an alkyl group (preferably having 1 to 40 carbon atoms, more preferably having 1 to 30 carbon atoms, particularly having 1 to 20 carbon atoms), alkenyl group (preferably having 2 to 40 carbon atoms, more preferably having 2 to 30 carbon atoms, particularly having 2 to 20 carbon atoms), alkynyl group (preferably having 2 to 40 carbon atoms, more preferably having 2 to 30 carbon atoms, particularly having 2 to 20 carbon atoms), aryl group (preferably having 6 to 30 carbon atoms, more preferably having 6 to 20 carbon atoms, particularly having 6 to 12 carbon atoms), substituted or unsubstituted amino group (preferably having 0 to 40 carbon atoms, more preferably having 0 to 30 carbon atoms, particularly having 0 to 20 carbon atoms), alkoxy group (preferably having 1 to 40 carbon atoms, more preferably having 1 to 30 carbon atoms, particularly having 1 to 20 carbon atoms), aryloxy group (preferably having 6 to 40 carbon atoms, more preferably having 6 to 30 carbon atoms, particularly having 6 to 20 carbon atoms), acyl group (preferably having 1 to 40 carbon atoms, more preferably having 1 to 30 carbon atoms, particularly having 1 to 20 carbon atoms), alkoxycarbonyl group (preferably having 2 to 40 carbon atoms, more preferably having 2 to 30 carbon atoms, particularly having 2 to 20 carbon atoms), aryloxycarbonyl group (preferably having 7 to 40 carbon atoms, more preferably having 7 to 30 carbon atoms, particularly having 7 to 20 carbon atoms), acyloxy group (preferably having 2 to 40 carbon atoms, more preferably having 2 to 30 carbon atoms, particularly having 2 to 20 carbon atoms), acylamino group (preferably having 2 to 40 carbon atoms, more preferably having 2 to 30 carbon atoms, particularly having 2 to 20 carbon atoms), alkoxycarbonylamino group (preferably having 2 to 40 carbon atoms, more preferably having 2 to 30 carbon atoms, particularly having 2 to 20 carbon atoms), aryloxycarbonylamino group (preferably having 7 to 40 carbon atoms, more preferably having 7 to 30 carbon atoms, particularly having 7 to 20 carbon atoms), sulfonylamino group (preferably having 1 to 40 carbon atoms, more preferably having 1 to 30 carbon atoms, particularly having 1 to 20 carbon atoms), sulfamoyl group (preferably having 0 to 40 carbon atoms, more preferably having 0 to 30 carbon atoms, particularly having 0 to 20 carbon atoms), carbamoyl group (preferably having 1 to 40 carbon atoms, more preferably having 1 to 30 carbon atoms, particularly having 1 to 20 carbon atoms), alkylthio group (preferably having 1 to 40 carbon atoms, more preferably having 1 to 30 carbon atoms, particularly having 1 to 20 carbon atoms), sulfonyl group (preferably having 1 to 40 carbon atoms, more preferably having 1 to 30 carbon atoms, particularly having 1 to 20 carbon atoms), sulfinyl group (sulfinyl group preferably having 1 to 40 carbon atoms, more preferably having 1 to 30 carbon atoms, particularly having 1 to 20 carbon atoms), ureido group (preferably having 1 to 40 carbon atoms, more preferably having 1 to 30 carbon atoms, particularly having 1 to 20 carbon atoms), phosphoric acid amide group (preferably having 1 to 40 carbon atoms, more preferably having 1 to 30 carbon atoms, particularly having 1 to 20 carbon atoms), hydroxy group, mercapto group, halogen atom (for example, fluorine atom, chlorine atom, bromine atom, iodine atom), cyano group, sulfo group, carboxyl group, nitro group, hydroxamic acid group, sulfino group, hydrazino group, imino group, heterocyclic group (preferably having 1 to 30 carbon atoms, more preferably having 1 to 12 carbon atoms, and typically containing hetero atom(s) such as nitrogen atom, oxygen atom and sulfur atom), and silyl group (preferably having 3 to 40 carbon atoms, more preferably having 3 to 30 carbon atoms, particularly having 3 to 24 carbon atoms). Each of these substituents may further be substituted by any of these substituents. If there are two or more substituents, they may be same or different. If possible, they may combine with each other to form a ring.

The divalent linking group independently represented by $X^{111}$, $X^{121}$ and $X^{131}$ is preferably a divalent linking group selected from the group consisting of alkylene group, alkenylene group, divalent aromatic group, divalent heterocyclic residue, —CO—, —$NR^a$— ($R^a$ represents an alkyl group having 1 to 5 carbon atoms, or hydrogen atom), —O—, —S—, —SO—, —SO—, and combination of any of them. The divalent linking group is more preferably a group combining at least two divalent groups selected from the group consisting of alkylene group, phenylene group, —CO—, —$NR^a$—, —O—, —S—, —$SO_2$—, and combination of any of them. The alkylene group preferably has 1 to 12 carbon atoms. The alkenylene group preferably has 2 to 12 carbon atoms. The divalent aromatic group preferably has 6 to 10 carbon atoms. Each of the alkylene group, alkenylene group and divalent aromatic group may be, if possible, substituted by any of the groups exemplified above as the substituents on $R^1$ to $R^4$ (e.g., alkyl group, halogen atom, cyano group, alkoxy group, acyloxy group).

Details and preferable scope of Formula (1) are described in paragraphs [0253] to [0276] of JP-B2-5566178, the contents of which are incorporated into this specification.

Details of Formula (2) and Formula (3) are described in paragraphs [0277] to [0286] of JP-B2-5566178, the contents of which are incorporated into this specification. Specific Examples of the compounds represented by Formulae (1), (2) and (3) are described in paragraphs [0287] to [0292] of JP-B2-5566178, the contents of which are incorporated into this specification.

In this invention, amount of consumption of the horizontal alignment agent is preferably 0.01 to 20% by mass, more preferably 0.05 to 10% by mass, and particularly 0.1 to 5% by mass, relative to the mass of compound represented by Formula (I) or Formula (II). Only a single species of the horizontal alignment agent may be used, or two or more species thereof may be used in combination. When two or more species are used in combination, the total content preferably falls in the above-described ranges.

[Anisotropic Light Absorption Film]

The anisotropic light absorption film of this invention is a film which contains the above-described coloring composition of this invention.

One example of the method of manufacturing the anisotropic light absorption film of this invention comprises at least the steps below in this order:

1) coating the coloring composition of this invention over a substrate, or over an alignment film preliminarily formed on the substrate, to thereby form a coating film;
2) heating the coating film, at or above the temperature at which all liquid crystalline components contained in the coating film cause transition to the liquid crystal phase; and
3) cooling the heated coating film down to room temperature.

In step 1), a coloring composition containing at least a single species of compound of this invention is prepared in the form of solution (coating liquid), and the coating liquid is coated over the surface to form a coating film. Method of coating is selectable from known methods including spin coating, gravure printing, flexographic printing, ink jet process, die coating, slot die coating, cap coating and dipping. Since it is typical to coat a solution diluted with an organic solvent, the coating is followed by drying, to obtain the coating film.

In step 2), the organic solvent or the like is evaporated off from the coated composition, then the coating film is heated to align the composition. Temperature of heating is preferably set at or above the temperature at which all liquid crystalline components contained in the coating film cause transition to the liquid crystal phase. Now, "the temperature at which all liquid crystalline components cause transition to the liquid crystal phase" means the highest temperature among the liquid crystal phase transition temperatures of the individual components in the composition, or, for the case where the components are mixed uniformly, it means the liquid crystal phase transition temperature of the mixture. The evaporation of organic solvent or the like from the coated composition may occur at the same time with the heating up to the above-described temperature.

In step 3), the heated film is cooled down to room temperature, to thereby fix the state of alignment. For the purpose of improving the heat resistance and durability, a polymerizable monomer and a polymerization initiator may be added to the composition, and prior to step 3), a polymerization reaction may be allowed to proceed to cure the film.

The anisotropic light absorption film (polarizing film) may be formed as described above. The anisotropic light absorption film is preferably 0.01 to 2 μm thick, more preferably 0.05 to 1 μm thick, and even more preferably 0.1 to 0.5 μm thick.

[Alignment Film]

The anisotropic light absorption film of this invention is preferably manufactured by using an alignment film. In other words, the anisotropic light absorption film of this invention is preferably formed on the surface of the alignment film. Also a laminate, which contains the alignment film and the anisotropic light absorption film of this invention, falls in the scope of this invention.

The alignment film used in this invention may be any kind of layer so long as it can align thereon molecules of the compound represented by Formula (I) or Formula (II) in a desired manner. The alignment film may be provided by any means including rubbing of the surface of an organic compound (preferably polymer) film, oblique deposition of an inorganic compound, formation of a layer having microgrooves, and building up of an organic compound (e.g., ω-tricosanoic acid, dioctadecylmethylammonium chloride, and methyl stearate) by the Langmuir-Blodgett (LB) method. There have been also known alignment films inducing an alignment function after applied with electric field, applied with magnetic field, or irradiated by light. Among them, the alignment film obtained by rubbing is preferable in this invention, from the viewpoint of easiness of controlling the pretilt angle of the alignment film. Also the photo-alignment film is preferable from the viewpoint of uniformity of alignment.

Rubbed Alignment Film

Polymer materials, used for forming the alignment film by rubbing, have been described in a number of literatures, and a number of products are commercially available. In this invention, polyvinyl alcohol or polyimide, and derivatives thereof are preferably used. As for the alignment film, the description from line 24 on page 43 to line 8 on page 49 of International Patent WO01/88574A1 may be referred to. The alignment film is preferably 0.01 to 10 μm thick, and more preferably 0.01 to 1 μm thick.

Photo-Alignment Film

Photo alignment materials, used for forming the alignment film by photo-irradiation, have been described in a number of literatures. In this invention, preferably exemplified are azo compounds described in JP-A-2006-285197, JP-A-2007-76839, JP-A-2007-138138, JP-A-2007-94071, JP-A-2007-121721, JP-A-2007-140465, JP-A-2007-156439, JP-A-2007-133184, JP-A-2009-109831, JP-B2-3883848 and JP-B2-4151746; aromatic ester compound described in JP-A-2002-229039; maleimide and/or alkenyl-substituted nadiimide compounds containing photo-alignment unit described in JP-A-2002-265541 and JP-A-2002-317013; photo-crosslinkable silane derivatives described in JP-B2-4205195 and JP-B2-4205198; and photo-crosslinkable polyimide, polyamide, or ester described in JP-T2-2003-520878, JP-T2-2004-529220 and JP-B2-4162850. The azo compounds, photo-crosslinkable polymide, polyamide, and ester are particularly preferable.

The photo-alignment film is manufactured by irradiating a film made of any of the above-described materials with linearly polarized light or non-polarized light.

In this specification, "irradiation with linearly polarized light" and "irradiation of non-polarized light" are operations for inducing photo-reaction in the photo-alignable material. Wavelength of light to be irradiated varies depending on the photo-alignable material to be used, and is not specifically limited so long as the wavelength is necessary for the photo-reaction. The light used for photo-irradiation preferably has a peak wavelength of 200 nm to 700 nm, and is more preferably UV light having a peak wavelength of 400 nm or shorter.

Light source used for photo-irradiation is exemplified by those widely used, including lamps such as tungsten lamp, halogen lamp, xenon lamp, xenon flash lamp, mercury lamp, mercury-xenon lamp and carbon are lamp; a variety of lasers [e.g., semiconductor laser, helium neon laser, argon ion laser, helium cadmium laser, YAG (yttrium aluminum garnet) laser]; light emitting diode; and cathode ray tube.

Means for obtaining linearly polarized light include a method of using a polarizing plate (e.g., iodine-containing polarizing plate, dichroic dye-containing polarizing plate, wire grid polarizing plate), a method of using a reflective polarizer making use of a prism element (e.g., Glan-Thompson prism), or based on incidence at the Brewster's angle and a method of using light emitted from a polarized laser light source. Alternatively, only light of necessary wavelength may be irradiated selectively through a filter, a wavelength converter or the like.

When the light to be irradiated is linearly polarized light, the light is made incident on the alignment film from the top or back, and vertically or obliquely to the surface of the alignment film. Angle of incidence of light is typically 0 to 90° (vertical), and preferably 40 to 90°, although it may vary depending on the photo-alignable material.

When the light to be irradiated is non-polarized light, the non-polarized light is made obliquely incident on the alignment film. The angle of incidence is 10 to 80°, preferably 20 to 60°, and particularly 30 to 50°.

Irradiation time is preferably 1 minute to 60 minutes, and more preferably 1 minute to 10 minutes.

If patterning is necessary, usable is a method of repeating photo-irradiation though photomask(s), a necessary number of times for patterning, and a method of drawing a pattern by scanning laser beam.

[Substrate]

The anisotropic light absorption film may be formed on a substrate. The substrate usable in this invention is selectable depending on the purpose of use of the anisotropic light absorption film. For example, polymer film may be used.

The substrate preferably has a light transmittance of 80% or larger. The substrate is preferably configured by using an optically isotropic polymer film. As for specific examples and preferred embodiments of the polymer, the description in paragraphs [0013] of JP-A-2002-22942 may be referred to. Even conventionally-known polymers such as polycarbonate and polysulfone, which are likely to exhibit birefringence, may be used, after suppressing the exhibition by molecular modification as described in International Patent WO/2000/26705.

In a laminate 100 illustrated in FIG. 1, an alignment film 103 is arranged on the surface of a substrate 102, and an anisotropic light absorption film 104 is arranged on the surface of the alignment film 103 (on the surface opposite to the substrate side).

[Intended Use of Anisotropic Light Absorption Film]

The anisotropic light absorption film of this invention can function, based on its anisotropy of light absorption, as a polarizing film through which linearly polarized light, circularly polarized light, elliptically polarized light and so forth is obtainable; can be functionalized to give a variety of anisotropic films having refractive index anisotropy, conduction anisotropy and so forth, by properly selecting the film forming process, the base, and the dye-containing composition; and can therefore give a variety of polarizing plates versatile for various applications. In short, according to this invention, there is provided a polarizing plate containing at least the anisotropic light absorption film of this invention or the laminate.

Figure 2:
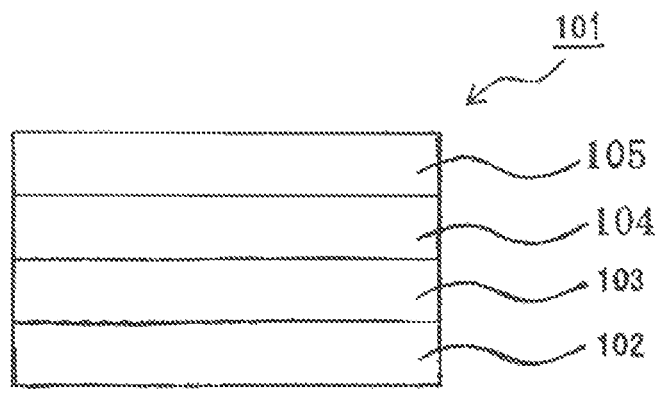
FIG. 2 illustrates an exemplary polarizing plate containing the anisotropic light absorption film of this invention.

In a polarizing plate 101 illustrated in FIG. 2, the alignment film 103 is arranged on the surface of the substrate 102, the anisotropic light absorption film 104 is arranged on the surface of the alignment film 103 (on the surface opposite to the substrate 102 side), and a retardation plate 105 is arranged on the surface of the anisotropic light absorption film 104 (on the surface opposite to the alignment film 103 side).

For the case where the anisotropic light absorption film of this invention is formed on the base and used as the polarizing plate, the thus-formed anisotropic light absorption film may be used solely by itself or may be used as a laminate after laminated, typically by wet film forming, with any of variously functionalized layers such as protection layer described above; adhesion layer, anti-reflection layer, alignment film; and optically functionalized layers including those functionalized as retardation film, as brightness enhancement film, as reflection film, as semi-transmissive reflection film, as diffusion film, and as optically-compensatory film.

The layers having these optical functions may be formed typically by the methods below.

The layer which functions as a retardation film may be formed typically by stretching as described for example in JP-B2-2841377 and JP-B2-3094113, or by a process described for example in JP-B2-3168850. The layer may be formed by coating and aligning whatever kind of liquid crystalline compound.

The layer which functions as a brightness enhancement film may be formed typically by forming micro-holes according to the methods described in JP-A-2002-169025 and JP-A-2003-29030, or, by laminating two or more cholesteric liquid crystal layers having different center wavelengths of selective reflection.

The layer which functions as a reflection film or semi-transmissive reflection film may be formed by using a metal thin film obtained by evaporation or sputtering.

The layer which functions as a diffusion film may be formed by coating, over the above-described protection layer, a resin solution which contains microparticles.

According to one embodiment of this invention, there is provided a circular polarizing plate which contains the anisotropic light absorption film of this invention. The circular polarizing plate has, laminated therein, the anisotropic light absorption film of this invention, and a layer which functions as the retardation film. The layer which functions as the retardation film is preferably a so-called quarter wave plate. The circular polarizing plate preferably has a (retardation (Re)/wavelength) value of 0.2 to 0.3 at 550 nm wavelength. The (retardation (Re)/wavelength) value is preferably 0.2 to 03 at 450 nm, 550 nm and 650 nm wavelengths, more preferably 0.23 to 0.27 at least at these three wavelengths, and even more preferably 024 to 0.26 at least at these three wavelengths. In short, the circular polarizing plate preferably has a (retardation (Re)/wavelength) value of 0.2 to 03, over a wide wavelength ranging from 450 nm to 650 nm, typically at 450 nm, 550 nm and 650 nm wavelengths.

The layer which functions as a retardation film may exhibit the optical properties by a monolayer configuration, or by a multilayer configuration.

[Image Display Device]

The image display device of this invention has the anisotropic light absorption film of this invention, a laminate or polarizing plate, and a display element (e.g., liquid crystal cell, and organic EL (electroluminescence) display panel).

Display element used for the image display device of this invention is exemplified, without special limitation, by liquid crystal cell, organic EL display panel, and plasma display panel. Among them, preferable are liquid crystal cell and organic EL display panel, and more preferable is organic EL display panel. Summarizing the above, the image display device of this invention is preferably a liquid crystal display device using a liquid crystal cell as the display element, or an organic EL display device using an organic EL display panel as the display element. The organic EL display device is more preferable.

<Liquid Crystal Cell>

The liquid crystal cell used for the liquid crystal display device of this invention is preferably based on, but not limited to, VA (Vertical Alignment) mode, OCB (Optically Compensated Bend) mode, IPS (In-Plane Switching) mode or TN (twisted nematic) mode.

<Organic EL Display Panel>

The organic EL display panel, as one preferred example of the image display device of this invention, is configured by using an organic EL element having an organic electroluminescence layer held between the electrodes (cathode and anode).

Configuration of the organic EL display panel may be any of known configurations, without special limitation.

Figure 3:
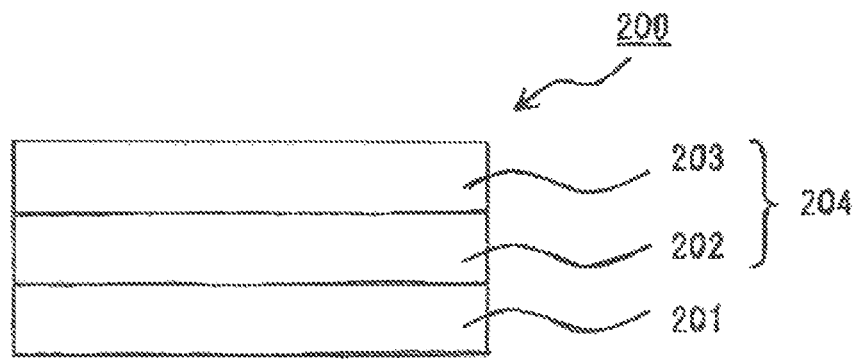
FIG. 3 illustrates an organic EL (electroluminescence) display device as an example of the image display device of this invention.

An organic EL display device 200 illustrated in FIG. 3 has a circular polarizing plate 204 having a quarter-wave plate 202 and an anisotropic light absorption film (polarizing film) 203, which is arranged on the viewer's side of an organic EL panel 201. The anisotropic light absorption film (polarizing film) 203 may have a protective film and/or functional layer formed thereon.

This invention will further be detailed below, referring to Examples. All materials, amounts of consumption, ratios, process details, process procedures and so forth explained in Examples below may be modified without departing from the spirit of this invention. The scope of this invention should therefore not be interpreted narrowly on the basis the specific Examples below.

Note that, Et in reaction formulae in Examples represents an ethyl group, and n-Bu represents a n-butyl group.

DMSO stands for dimethyl sulfoxide.

EXAMPLE

In Examples, optical characteristics of the anisotropic light absorption film were measured as described below.

<Dichroic Ratio>

Dichroic ratio was calculated according to the equation below, where the absorbance of the anisotropic light absorption film was measured using a spectrophotometer having an iodine-containing polarizing element arranged in the incident optical system:

$$\text{Dichroic ratio}(D)=Az/Ay$$

where,

Az: absorbance of incident polarized light by anisotropic light absorption film in the direction of absorption axis; and Ay: absorption of incident polarized light by anisotropic light absorption film in the direction of polarization axis.

Measurement conditions of the wavelength of maximum absorbance, proton NMR (Nuclear Magnetic Resonance) and mass spectrometry are summarized as below:

<Wavelength of Maximum Absorbance>

The wavelength of maximum absorbance in this invention was defined as the wavelength at which the transmitted light was minimized, when the transmission spectrum was measured in the ambient atmosphere at room temperature, using a spectrophotometer UV3100 (from Shimadzu Corporation) over the range from 400 to 800 nm.

<Proton NMR>

Proton NMR peaks in this invention were measured using Avance III (400 MHz) from Broker Corporation, at room temperature.

<Mass Spectrometry>

Mass spectrometric values in this invention were measured using hp1200/G1956B from Agilent.

Exemplary Synthesis 1

Synthesis of Compound No. 1

Synthetic Route of Compound No. 1

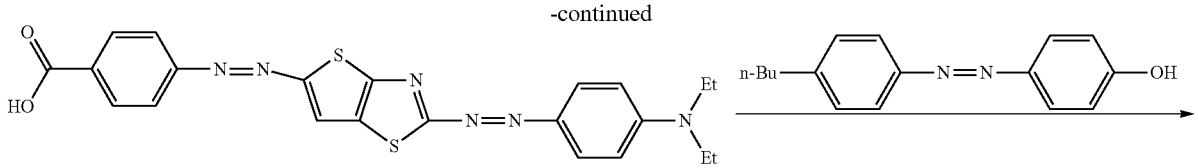

No. 1

Step 1

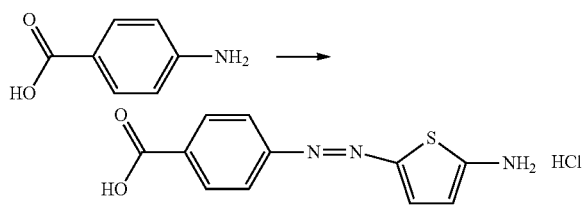

Source intermediate A

2-Aminothiophene was synthesized according to the method described in a literature (*Journal of Medicinal Chemistry*, 2005, Vol. 48, p. 5794), started from 2-nitrothiophene (from Wako Pure Chemical Industries, Ltd.).

1.1 g of paraaminobenzoic acid (from Tokyo Chemical Industry Co., Ltd.) was added to 9 ml of a 12 mol/L chloric acid solution, and the mixture was cooled so as to adjust the inner temperature to 0° C. or below. 5 ml of an aqueous solution containing 0.7 g of sodium nitrite (from Wako Pure Chemical Industries, Ltd.) was added dropwise therein. The mixture was stirred at an inner temperature of 0° C. for one hour, to prepare a diazonium solution. Next, the above-prepared diazonium solution was added dropwise into 10 ml of a methanol solution containing 1.0 g of 2-aminothiophene at an inner temperature of 0° C. The reaction solution was warmed up to room temperature, and stirred for two hours. The deposited solid was separated by filtration, and then dried, to obtain 1.10 g of source intermediate A of interest as an orange solid.

NMR data (DMSO-d6): δ 6.20 (d, 1H), 7.10 (d, 1H), 7.54 (d, 2H), 8.21 (d, 2H), 12.0 (s, 1H)

Step 2

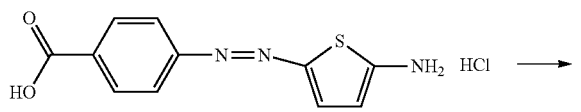

Source intermediate A

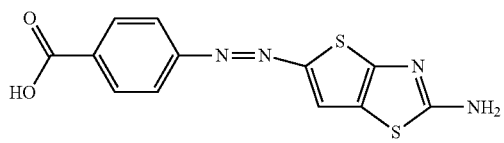

Source intermediate B

To a solution prepared by dissolving 0.60 g of source intermediate A into 10 ml of acetic acid, 0.40 g of sodium thiocyanate was added at room temperature, followed by dropwise addition of 2 ml of an acetic acid solution containing 0.10 ml of bromine. The mixture was stirred at room temperature for two hours, 10 ml of water was added thereto, the obtained solid was separated by filtration and rinsed with methanol, to thereby obtain 0.80 g of source intermediate B of interest as a red solid.

NMR data (DMSO-d6): δ 6.9 (s, 2H), 7.15 (s, 1H), 7.50 (d, 2H), 8.20 (d, 2H), 12.0 (s, 1H)

Step 3

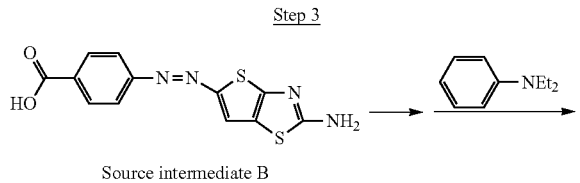

Source intermediate B

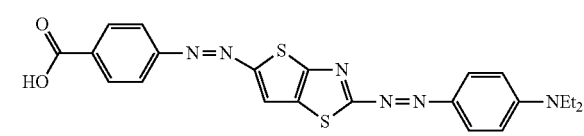

Source intermediate C 0.34 g of sodium nitrite was added portionwise to a solution of 2 ml of an hydrochloric acid and 2 ml of acetic acid which contains 1.5 g of source intermediate B under ice cooling, and the mixture was stirred for one hour. Then, 0.1 g of amidosulfuric acid was added thereto to prepare a diazonium salt of source intermediate B. The above-prepared diazonium salt solution was added dropwise to 10 mL of a methanol solution containing 0.8 g of diethylaniline (from Tokyo Chemical Industry Co., Ltd.) under ice cooling, and the mixture was stirred for one hour. Water was then added to the mixture, and the obtained solid was separated by filtration and rinsed with methanol, to thereby obtain 1.6 g of source intermediate C of interest as a blackish purple solid.

NMR data (DMSO-d6): δ 120 (t, 6H), 3.65 (d, 4H), 6.85 (d, 2H), 7.25 (s, 1H), 7.50 (d, 2H), 7.55 (d, 2H), 820 (d, 2H), 12.0 (s, 1H)

Step 4

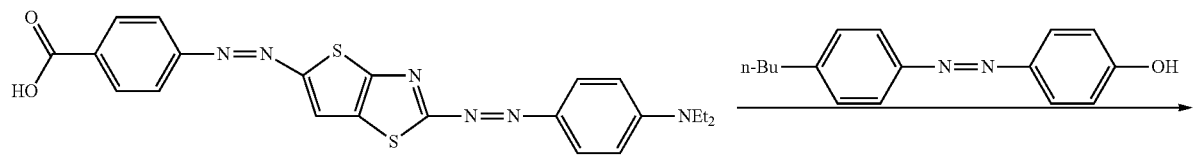

Source intermediate C → No1

4-Butylphenylazophenol, used as the source material, was purchased from Tokyo Chemical Industry Co., Ltd.

20 mg of dimethylaminopyridine (from Tokyo Chemical Industry Co., Ltd.) and 0.22 g of dicyclohexylcarbodiimide (from Tokyo Chemical Industry Co, Ltd.) were added dropwise to 10 ml of a methylene chloride solution containing 0.46 g of source intermediate C and 0.25 g of 4-butylphenylazophenol (from Tokyo Chemical Industry Co., Ltd.) at room temperature, and the mixture was stirred for 2 hours. Water was then added to the mixture, organic matters wee extracted with ethyl acetate, the solvent was evaporated off under reduced pressure, and the residue was purified by silica gel column chromatography (eluent: hexane+chloroform), to thereby obtain 0.45 g of compound No. 1 of interest as a green solid.

NMR data (DMSO-d6): δ 0.95 (t, 3H), 1.25 (m, 8H) 1.50 (m, 2H), 2.90 (d, 2H), 3.68 (d, 4H), 6.85 (d, 2H), 7.25 (s, 1H), 7.50 (m, 4H), 7.55 (m, 4H), 7.90 (d, 2H), 8.20 (d, 2H), 8.60 (d, 2H)

Mass spectrometry: molecular ion (M+)=701

Exemplary Synthesis 2

Synthesis of Compound No. 14

Synthetic Route of Compound No. 14

Step 1

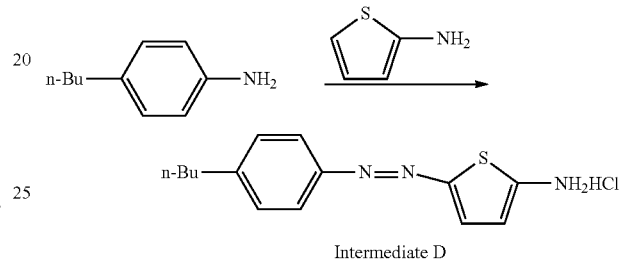

Intermediate D 12 g of 4-butylaniline (from Tokyo Chemical Industry Co, Ltd.) was added to 9 ml of a 12 mol/L hydrochloric acid solution, and the mixture was cooled so as to adjust the inner temperature to 0° C., to which 5 ml of an aqueous solution containing 0.7 g of sodium nitrite (from Wako Pure Chemical Industries, Ltd.) was added dropwise thereto. The mixture was stirred at an inner temperature of 0° C. for one hour, to prepare a diazonium solution. Next, to 10 ml of a methanol solution containing 1.0 g of 2-aminothiophene, the above prepared diazonium solution was added dropwise at an inner temperature of 0° C. The reaction solution was warmed up to room temperature, and stirred for 2 hours. The

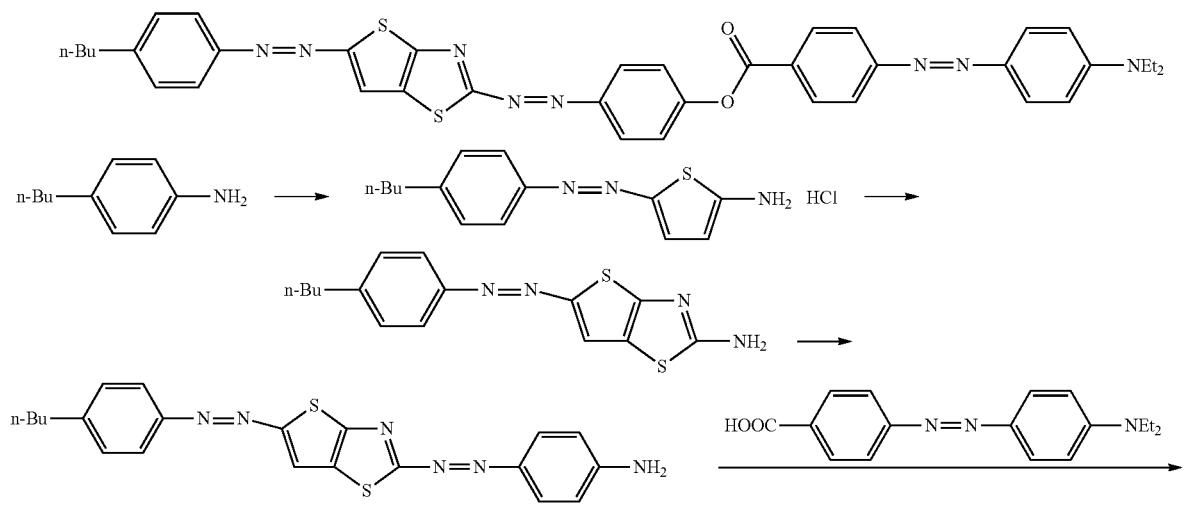

No. 1 deposited solid was separated by filtration and dried, to thereby obtain 1.30 g of source intermediate D of interest as an orange solid.

NMR data (DMSO-d6): δ 0.91 (t, 3H), 138 (m, 2H), 1.76 (m, 2H), 2.80 (m, 2H), 6.18 (d, 1H), 7.05 (d, 1H), 7.50 (d, 2H), 831 (d, 2H)

Step 2

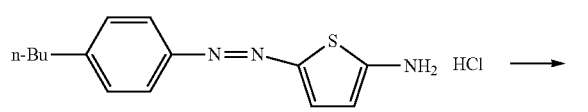

Source intermediate D

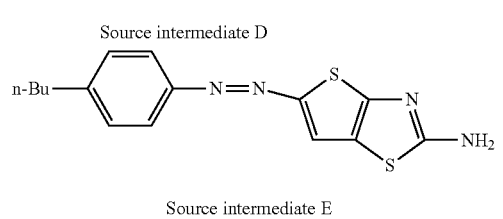

Source intermediate E 0.80 g of source intermediate D was dissolved into 10 ml of acetic acid, and 0.45 g of sodium thiocyanate was added thereto at room temperature, followed by dropwise addition of 3 ml of an acetic acid solution containing 0.11 ml of bromine. The mixture was stirred at room temperature for 2 hours, to which 10 ml of water was added, and the obtained solid was separated by filtration and rinsed with methanol, to thereby obtain 0.90 g of source intermediate E of interest as a red solid.

NMR data (DMSO-d6): δ 0.90 (t, 3H), 130 (m, 2H), 1.75 (m, 2H), 2.60 (m, 2H), 6.80 (s, 2H), 7.15 (s, 1H), 7.50 (d, 2H), 8.20 (d, 2H)

Step 3

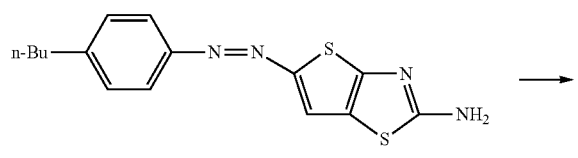

Source intermediate E

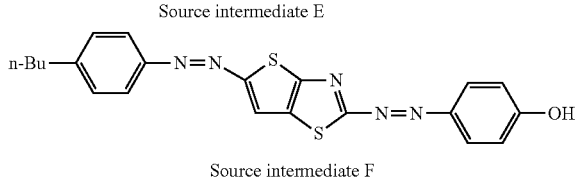

Source intermediate F 0.36 g of sodium nitrite was added portionwise into a solution of 2 ml of a hydrochloric acid and 2 ml of acetic acid which contains 1.6 g of source intermediate E under ice cooling, and the mixture was stirred for 1 hour. 0.1 g of amidosulfuric acid was added thereto to prepare a diazonium salt of source intermediate E. The above obtained diazonium salt solution was added dropwise into 10 ml of a methanol solution containing 0.60 g of phenol (from Tokyo Chemical Industry Co., Ltd.) under ice cooling, and the mixture was stirred for 1 hour Water was added to the mixture, and the obtained solid was separated by filtration and rinsed with methanol, to thereby obtain 1.45 g of source intermediate F of interest as a purplish red solid.

NMR data (DMSO-d6): δ 0.90 (t, 3H), 130 (m, 2H), 1.75 (m, 2H), 2.60 (m, 2H), 6.80 (d, 2H), 728 (s, 1H), 7.35 (d, 2H), 7.55 (d, 2H), 820 (d, 2H)

Exemplary Synthesis 2

Step 4

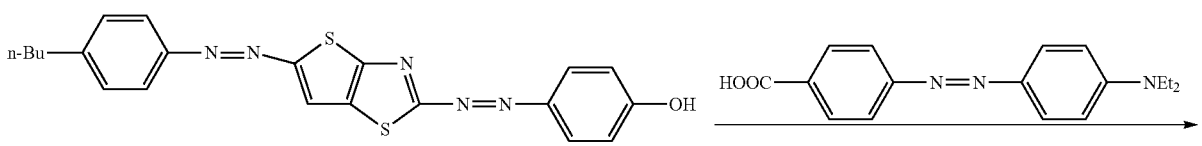

Source Intermediate F 4-(4-Diethylamino-phenylazo)benzoic acid, used as the source material, was synthesized according to the method described in a literature (Archiv der Pharmazie (Weinheim, Germany), 1915, Vol. 253, p. 372).

15 mg of dimethylaminopyridine (from Tokyo Chemical Industry Co., Ltd.) and 0.25 g of dicyclohexylcarbodiimide (from Tokyo Chemical Industry Co., Ltd.) were added dropwise to 10 ml of a methylene chloride solution containing 0.55 g of source intermediate F and 0.30 g of 4-(4-diethylamino-phenylazo)benzoic acid at room temperature, and the mixture was stirred for 2 hours. Water was added to the mixture, organic matters were extracted into ethyl acetate, the solvent was evaporated off under reduced pressure, and the residue was purified by silica gel column chromatography (eluent:hexane+chloroform), to thereby obtain 0.42 g of compound No. 14 of interest as a green solid.

NMR data (DMSO-d6) δ 0.95 (t, 3H), 1.25 (m, 8H), 1.52 (m, 2H), 2.80 (d2H), 3.60 (d, 4H), 6.90 (d, 2H), 7.32 (s, 1H), 7.5-6 (m, 8H), 7.95 (d, 2H), 8.10 (d, 2H), 8.56 (d, 2H)

Mass spectrometry: molecular ion (M+)=701

Example 1

Compound No. 1 of this invention (2 parts by mass) was added to chloroform (98 parts by mass), and dissolved therein by stirring, to thereby obtain a coating liquid for forming anisotropic light absorption film. The coating liquid was spin-coated over a polyvinyl alcohol alignment film (PVA-103 (trade name) from Nissan Chemical Industries, Ltd.) preliminarily formed on a glass substrate and rubbed to induce homogeneous alignment, allowed to dry naturally, and heated at 70° C. for one minute, to obtain an anisotropic light absorption film. The film was found to be 02 μm thick. The obtained anisotropic light absorption film was found to have a dichroic ratio of 20.

Comparative Example 1

Comparative Dye (H-1) (2 parts by mass) was added to chloroform (98 parts by mass), and dissolved under stirring, and thereby a coating liquid for forming anisotropic light absorption film was obtained. The coating liquid was spin-coated over a polyvinyl alcohol alignment film (PVA-103 (trade name) from Nissan Chemical Industries, Ltd.) preliminarily formed on a glass substrate and rubbed to induce homogeneous alignment, allowed to dry naturally, and heated at 70° C. for one minute, to obtain an anisotropic light absorption film. The film was found to be 0.2 μm thick. The obtained anisotropic light absorption film was found to have a dichroic ratio of 17.
Comparative Dye (H-1)

forming anisotropic light absorption film. The coating liquid was spin-coated over a polyvinyl alcohol alignment film (PVA-103 (trade name) from Nissan Chemical Industries, Ltd.) preliminarily formed on a glass substrate and rubbed to induce homogeneous alignment, allowed to dry naturally, and heated at 70° C. for one minute, to obtain an anisotropic light absorption film. The film was found to be 0.2 μm thick. The obtained anisotropic light absorption film was found to have a dichroic ratio of 20.

Example 3

Dye C-23 (wavelength of maximum absorbance=455 nm) (1.00 parts by mass) below, compound No. 1 of this invention (1.00 part by mass), and liquid crystalline polymer PB-17 (number-average molecular weight (Mn)=137,000, liquid crystal phase-isotropic phase transition temperature (Ti)=320° C.) (2.00 parts by mass) were dissolved into chloroform (396 parts by mass) to prepare a coating liquid. In the solid content of the coating liquid, content by mass of the dichroic dye was 50% by mass.

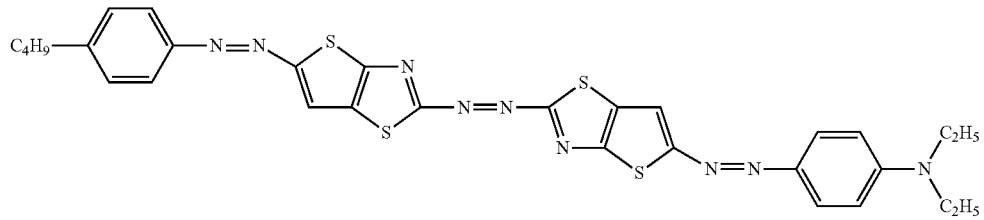

Comparative Example 2

An anisotropic light absorption film was obtained in the same way as in Comparative Example 1, except that Comparative Dye (H-2) was used in place of Comparative Dye (H-1). The obtained anisotropic light absorption film was found to have a dichroic ratio of 15.
Comparative Dye (H-2)

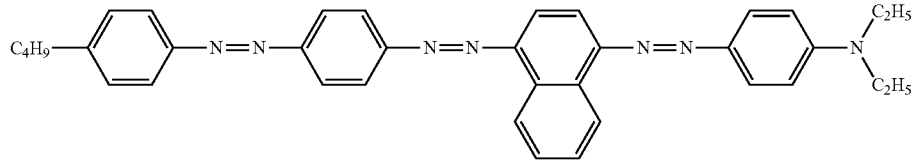

Example 2

Compound No. 14 of this invention (2 parts by mass) was added to chloroform (98 parts by mass), and dissolved therein by stirring, to thereby obtain a coating liquid for

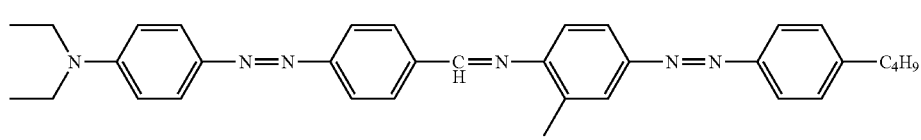

C-23

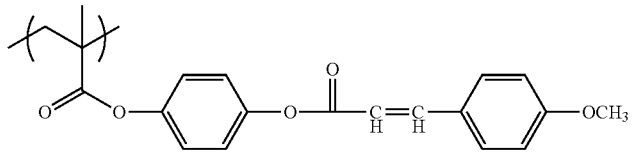

PB-17

The coating liquid was spin-coated over a rubbed polyimide alignment film RN1199 (from Nissan Chemical Industries, Ltd.), to form a coating film of 0.2 μm thick. The coating film was heated for 20 seconds on a hot plate heated to 230° C., and then cooled down to room temperature. The obtained anisotropic light absorption film was found to have a very uniform surface profile, with a dichroic ratio of 32.0. In order to evaluate heat resistance of the anisotropic light absorption film, the film was allowed to stand in an atmosphere at 80° C. for 24 hours. The dichroic ratio was determined to be 31.8, proving almost no degradation of the dichroic ratio.

Example 4

Dye C-24 (wavelength of maximum absorbance=460 nm) shown below (1.00 parts by mass), compound No. 1 of this invention (1.00 part by mass), and liquid crystalline polymer PB-17 (number-average molecular weight (Mn)=137,000, liquid crystal phase-isotropic phase transition temperature (Ti)=320° C.) shown below (2.00 parts by mass) were dissolved into chloroform (396 parts by mass), to prepare a coating liquid. In the solid content of the coating liquid, content by mass of the dichroic dye was 50% by mass.

The coating liquid was spin-coated over a rubbed polyimide alignment film RN1199 (from Nissan Chemical Industries, Ltd.), to form a coating film of 0.2 μm thick. The coating film was heated for 20 seconds on a hot plate heated to 230° C., and then cooled down to room temperature. The obtained anisotropic light absorption film was found to have a very uniform surface profile, with a dichroic ratio of 34.0. In order to evaluate heat resistance of the anisotropic light absorption film, the film was allowed to stand in an atmosphere at 80° C. for 24 hours. The dichroic ratio was determined to be 34.0, proving no degradation of the dichroic ratio.

Example 5

Dye C-25 (wavelength of maximum absorbance=460 nm) shown below (1.00 parts by mass), compound No. 1 of this invention (1.00 parts by mass), and liquid crystalline polymer PB-17 (number-average molecular weight (Mn)=137,000, liquid crystal phase-isotropic phase transition tempera-

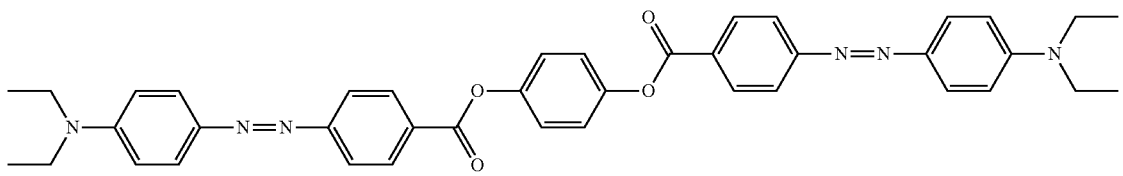

C-24

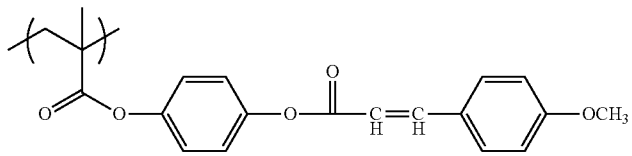

PB-17 ture (Ti)=320° C.) shown below (2.00 parts by mass) were dissolved into chloroform (396 parts by mass), to prepare a coating liquid. In the solid content of the coating liquid, content by mass of the dichroic dye was 50% by mass.

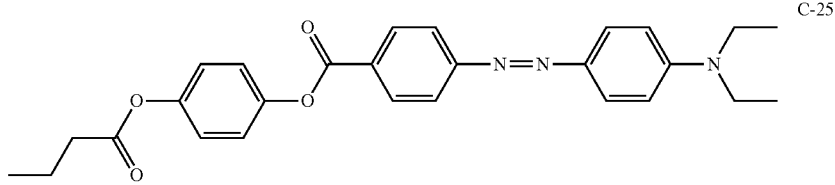

C-25

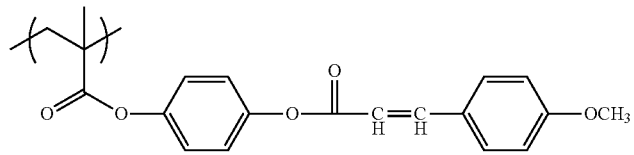

PB-17

The coating liquid was spin-coated over a rubbed polyimide alignment film RN1199 (from Nissan Chemical Industries, Ltd.), to form a coating film of 0.2 μm thick. The coating film was heated for 20 seconds on a hot plate heated to 230° C., and then cooled down to room temperature. The obtained anisotropic light absorption film was found to have a very uniform surface profile, with a dichroic ratio of 31.5. In order to evaluate heat resistance of the anisotropic light absorption film, the film was allowed to stand in an atmosphere at 80° C. for 24 hours. The dichroic ratio was determined to be 31.0, proving almost no degradation of the dichroic ratio.

Example 6

Dye C-24 (1.00 parts by mass) shown below and compound No. 1 of this invention (1.00 parts by mass) were dissolved into chloroform (398 parts by mass), to prepare a coating liquid.

hours. The dichroic ratio was determined to be 22.7. The dichroic ratio was found to be decreased.

Example 7

An experiment was conducted in the same way as in Example 3, except that liquid crystalline polymer PB-1 (number-average molecular weight (Mn)=3,400, liquid crystal phase-isotropic phase transition temperature (Ti)=320° C.), shown below, was used in place of liquid crystalline polymer PB-17. The obtained anisotropic light absorption film was found to have a very uniform surface profile, with a dichroic ratio of 34.1. In order to evaluate heat resistance of the anisotropic light absorption film, the film was allowed to stand in an atmosphere at 80° C. for 24 hours. The dichroic ratio was determined to be 33.8, proving almost no decrease in the dichroic ratio.

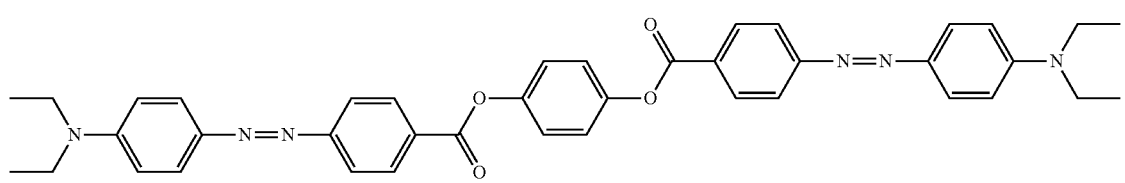

C-24

The coating liquid was spin-coated over a rubbed polyimide alignment film RN1199 (from Nissan Chemical Industries, Ltd., to form a coating film of 0.2 μm thick. The coating film was heated for 20 seconds on a hot plate heated to 230° C., and then cooled down to room temperature. The obtained anisotropic light absorption film was found to have a very uniform surface profile, with a dichroic ratio of 26.0. In order to evaluate heat resistance of the anisotropic light absorption film, the film was allowed to stand in an atmosphere at 80° C. for 24 hours. The dichroic ratio was determined to be 24.5, proving almost no degradation of the dichroic ratio.

Comparative Example 3

An experiment was conducted in the same way as in Example 3, except that Comparative Dye (H-1) was used in place of compound No. 1 of this invention. The coating film was heated on a hot plate heated to 230° C. for 20 seconds, and then cooled down to room temperature. The obtained anisotropic light absorption film was found to have a surface profile containing partial failure. The dichroic ratio at this time was determined to be 28.5. In order to evaluate heat resistance of the anisotropic light absorption film, the film was allowed to stand in an atmosphere at 80° C. for 24

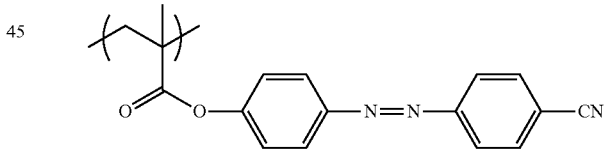

PB-1

Comparative Example 4

An experiment was conducted in the same way as in Comparative Example 3, except that the above-described liquid crystalline polymer PB-1 was used in place of liquid crystalline polymer PB-17. The obtained anisotropic light absorption film was found to have a surface profile containing partial failure. The dichroic ratio at this time was determined to be 30.5. In order to evaluate heat resistance of the anisotropic light absorption film, the film was allowed to stand in an atmosphere at 80° C. for 24 hours. The dichroic ratio was determined to be 26.0. The dichroic ratio was found to be decreased.

Example 8

An experiment was conducted in the same way as in Example 3, except that liquid crystalline polymer PB-23 (number-average molecular weight (Mn)=24,200, liquid crystal phase-isotropic phase transition temperature (Ti)=227° C.), shown below, was used in place of liquid crystalline polymer PB-17. The obtained anistropic light absorption film was found to have a very uniform surface profile, with a dichroic ratio of 34.4. In order to evaluate heat resistance of the anisotropic light absorption film, the film was allowed to stand in an atmosphere at 80° C. for 24 hours. The dichroic ratio was determined to be 34.2, proving almost no decrease in the dichroic ratio.

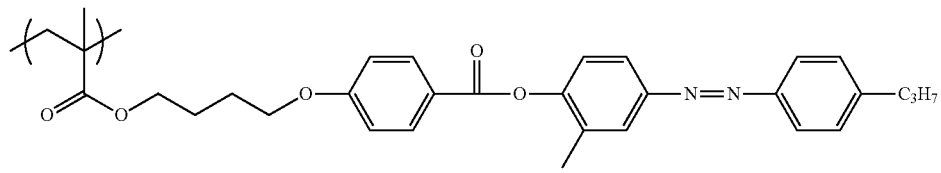

PB-23

Comparative Example 5

An experiment was conducted in the same way as in Comparative Example 3, except that the above-described liquid crystalline polymer PB-23 was used in place of liquid crystalline polymer PB-17. The obtained anisotropic light absorption film was found to have a surface profile containing partial failure. The dichroic ratio at this time was determined to be 31.0. In order to evaluate heat resistance of the anisotropic light absorption film, the film was allowed to stand in an atmosphere at 80° C. for 24 hours. The dichroic ratio was determined to be 27.2. The dichroic ratio was found to be decreased.

Example 9

An experiment was conducted in the same way as in Example 8, except that compound No. 14 of this invention was used in place of compound No. 1 of this invention. The obtained anisotropic light absorption film was found to have a very uniform surface profile, with a dichroic ratio of 32.0. In order to evaluate heat resistance of the anisotropic light absorption film, the film was allowed to stand in an atmosphere at 80° C. for 24 hours. The dichroic ratio was determined to be 31.8, proving almost no decrease in the dichroic ratio.

CONCLUSION

Results of the above-described Examples 1 to 9 and Comparative Examples 1 to 5 are summarized in Table below. It is understood that Examples using the dye of this invention successfully achieved high levels of dichroic ratio, showing only small decrease in the dichroic ratio even after stored. It is also understood that the coloring composition of this invention was excellent in compatibility with the yellow dye and magenta dye, since Examples 3 to 9 using the coloring composition of this invention showed very uniform surface profiles of the films.

TABLE 3

|  | Dye | Liquid crystalline polymer | Surface profile of film | Dichroic ratio as manufactured | Dichroic ratio after stored |
|---|---|---|---|---|---|
| Example 1 | Compound No. 1 | — | Not evaluated | 20 | Not measured |
| Comparative Example 1 | Comparative Dye (H-1) | — | Not evaluated | 17 | Not measured |
| Comparative Example 2 | Comparative Dye (H-2) | — | Not evaluated | 15 | Not measured |
| Example 2 | Compound No. 14 | — | Not evaluated | 20 | Not measured |

TABLE 3-continued

|  | Dye | Liquid crystalline polymer | Surface profile of film | Dichroic ratio as manufactured | Dichroic ratio after stored |
|---|---|---|---|---|---|
| Example 3 | Compound No. 1 and Dye C-23 | PB-17 | Very uniform | 32.0 | 31.8 |
| Example 4 | Compound No. 1 and Dye C-24 | PB-17 | Very uniform | 34.0 | 34.0 |
| Example 5 | Compound No. 1 and Dye C-25 | PB-17 | Very uniform | 31.5 | 31.0 |
| Example 6 | Compound No. 1 and Dye C-24 | — | Very uniform | 26.0 | 24.5 |
| Comparative Example 3 | Comparative Dye (H-1) and Dye C-23 | PB-17 | Partial failure | 28.5 | 22.7 |
| Example 7 | Compound No. 1 and Dye C-23 | PB-1 | Very uniform | 34.1 | 33.8 |
| Comparative Example 4 | Comparative Dye (H-1) and Dye C-23 | PB-1 | Partial failure | 30.5 | 26.0 |
| Example 8 | Compound No. 1 and Dye C-23 | PB-23 | Very uniform | 34.4 | 34.2 |
| Comparative Example 5 | Comparative Dye (H-1) and Dye C-23 | PB-23 | Partial failure | 31.0 | 27.2 |
| Example 9 | Compound No. 14 and Dye C-23 | PB-23 | Very uniform | 32.0 | 31.8 |

<Formation of Alignment Film 1>

On the surface of the anisotropic light absorption film manufactured in Example 8, alignment film 1 was formed by using a coating liquid for forming alignment film 1 below. The surface of the alignment film 1 was rubbed in the direction 45° away from the direction of rubbing of the alignment film given in the process of forming the anisotropic light absorption film.

| Composition of Coating Liquid for Forming Alignment Film 1 | |
|---|---|
| Modified polyvinyl alcohol, shown below | 2.4 parts by mass |
| Isopropanol | 1.6 parts by mass |
| Methanol | 36 parts by mass |
| Water | 60 parts by mass |

Modified polyvinyl alcohol

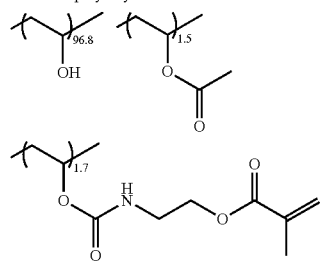

<Manufacture of Optically Anisotropic Layer 1>

Coating liquid 1 for forming optically anisotropic layer having the composition below, was prepared.

| Composition of Coating Liquid 1 for Forming Optically Anisotropic Layer | |
|---|---|
| Liquid crystalline compound R-3, showing reverse wavelength dispersion | 100 parts by mass |
| Photo-polymerization initiator (Irgacure (registered trademark) 819, from BASF) | 3.0 parts by mass |
| Fluorine-containing compound A | 0.8 parts by mass |
| Crosslinkable polymer O-2 | 0.3 parts by mass |
| Chloroform | 588 parts by mass |

Liquid crystalline compound R-3, showing reverse wavelength dispersion:

Specific Example II-3-9

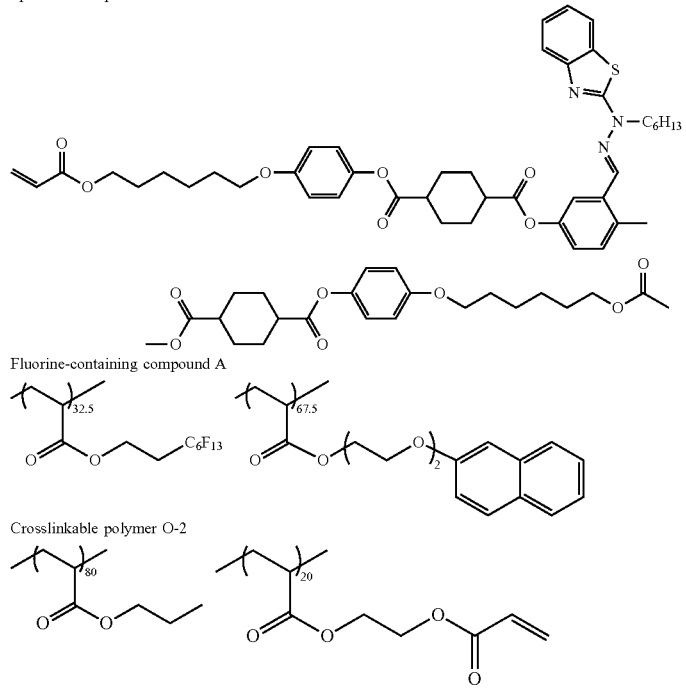

Fluorine-containing compound A

Crosslinkable polymer O-2

Over the surface of the rubbed alignment film 1 manufactured above, the coating liquid 1 for forming optically anisotropic layer was coated using a bar coater. The coating was ripened under heating at a film surface temperature of 100° C. for 60 seconds, then cooled down to 70° C. UV light of 1000 mJ/cm² was irradiated thereon in the air, using a 70 mW/cm² air-cooled metal halide lamp (from Eye Graphics Co., Ltd.) to fix the state of alignment, thereby an optically anisotropic layer 1 was formed.

The thus-manufactured optically anisotropic layer 1 was found to have in-plane retardation (Re) values at 450 nm, 550 nm and 650 nm wavelengths of 108 nm, 130 nm and 137 nm, respectively. Retardation (Rth) value in the width direction at 550 nm wavelength was 65 nm.

The thus-manufactured optical film was bonded to an organic EL element. Reflectivity in the black state was measured to be 3%. That is, the optical film of this invention was confirmed to be useful as an anti-reflection film for organic EL element

100 laminate
101 polarizing plate
102 substrate
103 alignment film
104 anisotropic light absorption film
105 retardation plate
200 organic EL display device
201 organic EL panel
202 quarter-wave plate
203 anisotropic light absorption film (polarizing film)
204 circular polarizing plate

What is claimed is:

1. An anisotropic light absorption film comprising: a coloring composition comprising one or more species of compounds represented by Formula (I) or Formula (II) below and one or more species of thermotropic liquid crystalline polymer:

Formula (I)
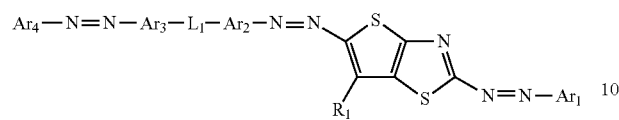

in Formula (I), $R_1$ represents a hydrogen atom or substituent, each of $Ar_1$, $Ar_2$, $Ar_3$ and $Ar_4$ independently represents an optionally substituted aromatic hydrocarbon group or optionally substituted heterocyclic group, and $L_1$ represents a divalent linking group which interrupts π electron conjugated system;

Formula (II)
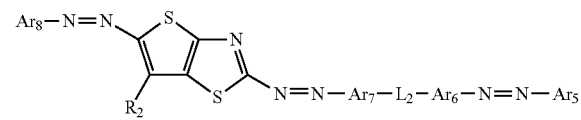

in Formula (II), $R_2$ represents a hydrogen atom or substituent, each of $Ar_5$, $Ar_6$, $Ar_7$ and $Ar_8$ independently represents an optionally substituted aromatic hydrocarbon group or optionally substituted heterocyclic group, and $L_2$ represents a divalent linking group which interrupts π electron conjugated system, wherein the thermotropic liquid crystalline polymer is in the form of side-chain polymer liquid crystal.

2. The anisotropic light absorption film of claim 1, wherein in Formula (I) and Formula (II), each of $R_1$ and $R_2$ represents a hydrogen atom.

3. The anisotropic light absorption film of claim 1, wherein in Formula (I) and Formula (II), each of $L_1$ and $L_2$ represents —O(C=O)—, —(C=O)O—, —O—, —CH$_2$—, or combination thereof.

4. The anisotropic light absorption film of claim 1, wherein the compound represented by Formula (I) or Formula (II) is a compound represented by Formula (IA) or (IIA) below:

Formula (IA)
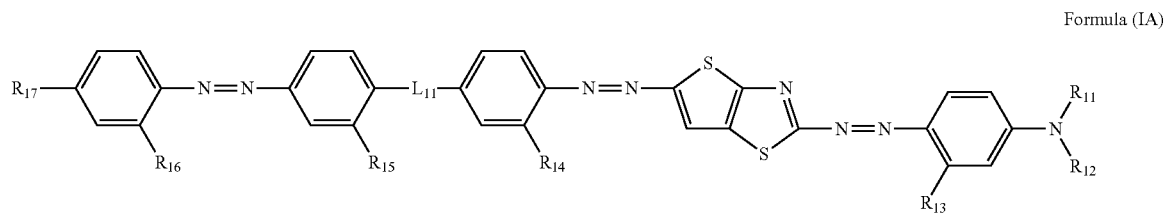

in Formula (IA), each of $R_{11}$ and $R_{12}$ independently represents an alkyl group having 1 to 6 carbon atoms or polymerizable group, each of $R_{13}$, $R_{14}$, $R_{15}$ and $R_{16}$ independently represents a hydrogen atom, alkyl group having 1 to 6 carbon atoms or alkoxy group having 1 to 6 carbon atoms, $R_{17}$ represents an alkyl group having 1 to 6 carbon atoms, alkoxy group having 1 to 6 carbon atoms, alkoxycarbonyl group having 2 to 6 carbon atoms, acyl group having 1 to 6 carbon atoms, or polymerizable group, and $L_{11}$ represents —O(C=O)—, —CH$_2$CH$_2$—, —CH$_2$O—, —(C=O)O—, or —O—;

Formula (IIA)
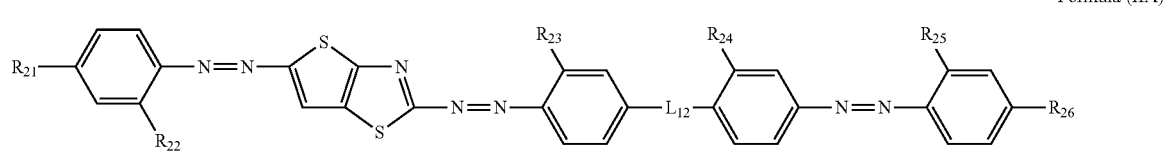

in Formula (IIA), $R_{21}$ represents $-N(R_{31})(R_{32})$, alkyl group having 1 to 6 carbon atoms, alkoxycarbonyl group having 2 to 6 carbon atoms, or polymerizable group, each of $R_{22}$, $R_{23}$, $R_{24}$ and $R_{25}$ independently represents a hydrogen atom, alkyl group having 1 to 6 carbon atoms or alkoxy group having 1 to 6 carbon atoms, $R_{26}$ represents an alkyl group having 1 to 6 carbon atoms, alkoxy group having 1 to 6 carbon atoms, alkoxycarbonyl group having 2 to 6 carbon atoms, or $-N(R_{41})(R_{42})$, and $L_{12}$ represents $-O(C=O)-$, $-CH_2CH_2-$, $-OCH_2-$, or $-(C=O)O-$, where each of $R_{31}$ and $R_{32}$ independently represents an alkyl group having 1 to 6 carbon atoms or polymerizable group, and each of $R_{41}$ and $R_{42}$ independently represents an alkyl group having 1 to 6 carbon atoms.

5. The anisotropic light absorption film of claim 1, further comprising one or more species of coloring compounds other than the compound represented by Formula (I) or Formula (II).

6. The anisotropic light absorption film of claim 5, wherein each of the one or more species of coloring compounds other than the compound represented by Formula (I) or Formula (II) have a wavelength of maximum absorbance of 400 to 600 nm.

7. The anisotropic light absorption film of claim 5, wherein each of the one or more species of coloring compounds other than the compound represented by Formula (I) or Formula (II) is a compound represented by Formula (III) or Formula (IV) below:

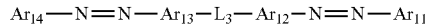

Formula (III)

in Formula (III), each of $Ar_{11}$, $Ar_{12}$, $Ar_{13}$ and $Ar_{14}$ independently represents an optionally substituted aromatic hydrocarbon group or optionally substituted heterocyclic group, and $L_3$ represents a divalent linking group,

Formula (IV)

in Formula (IV), each of $Ar_{15}$ and $Ar_{16}$ independently represents an optionally substituted aromatic hydrocarbon group or optionally substituted heterocyclic group.

8. The anisotropic light absorption film of claim 1, wherein the thermotropic liquid crystalline polymer is a polymer at least having a repeating unit represented by any one of Formulae (IX-a), (IX-b) and (IX-c) below:

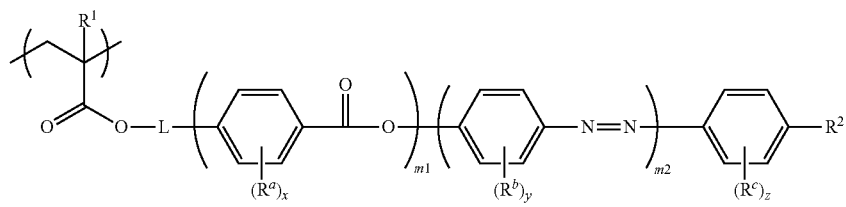

(IX-a)

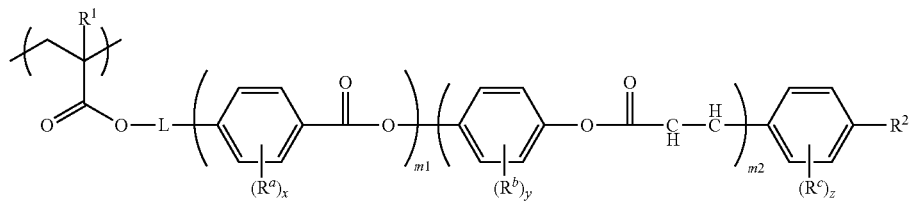

(IX-b)

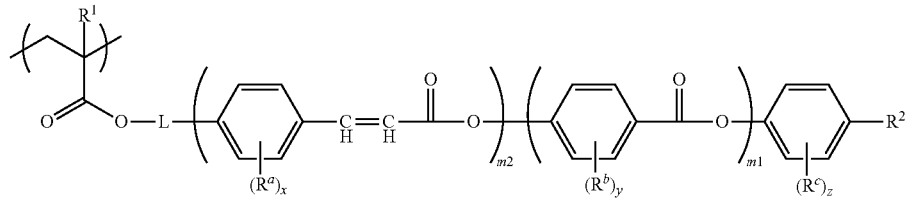

(IX-c)

in Formulae (IX-a), (IX-b) and (IX-c), $R^1$ represents a hydrogen atom or methyl group; L represents a single bond, $-(CH_2)_{x1}O-$ or $-(CH_2CH_2O)_{y1}-$, where x1 represents an integer of 2 to 10, y1 represents an integer of 1 to 5, $R^2$ represents a hydrogen atom, alkyl group having 1 to 10 carbon atoms, alkoxy group having 1 to 9 carbon atoms, cyano group, or optionally substituted amino group; m1 represents an integer of 0 to 2; m2 represents an integer of 1 to 2; each of $R^a$, $R^b$ and $R^c$ independently represents a substituent; and each of x, y and z independently represents an integer of 0 to 4.

9. The anisotropic light absorption film of claim 1, further comprising a horizontal alignment agent.

10. The anisotropic light absorption film of claim 1, which is formed on a surface of an alignment film.

11. A laminate comprising an alignment film and the anisotropic light absorption film of claim 1.

12. A polarizing plate comprising at least the anisotropic light absorption film of claim 1.

13. A polarizing plate comprising at least the laminate of claim 11.

14. An image display device comprising the anisotropic light absorption film of claim 1.

15. An image display device comprising the laminate of claim 11.

16. An image display device comprising the polarizing plate of claim 12.

17. An image display device comprising the polarizing plate of claim 13.

* * * * *